(12) United States Patent
Craig

(10) Patent No.: US 8,738,126 B2
(45) Date of Patent: *May 27, 2014

(54) SYNCHRONIZATION OF VAGUS NERVE STIMULATION WITH THE CARDIAC CYCLE OF A PATIENT

(75) Inventor: Arthur D. Craig, Phoenix, AZ (US)

(73) Assignee: Catholic Healthcare West, Phoenix, AZ (US)

( * ) Notice: Subject to any disclaimer, the term of this patent is extended or adjusted under 35 U.S.C. 154(b) by 465 days.

This patent is subject to a terminal disclaimer.

(21) Appl. No.: 12/401,026

(22) Filed: Mar. 10, 2009

(65) Prior Publication Data

US 2009/0177252 A1    Jul. 9, 2009

Related U.S. Application Data

(63) Continuation of application No. 11/693,499, filed on Mar. 29, 2007, now Pat. No. 8,219,188.

(60) Provisional application No. 60/787,680, filed on Mar. 29, 2006.

(51) Int. Cl.
   *A61N 1/36* (2006.01)

(52) U.S. Cl.
   USPC ................................. 607/2; 607/45

(58) Field of Classification Search
   USPC ............................ 607/2, 115–118
   See application file for complete search history.

(56) References Cited

U.S. PATENT DOCUMENTS

| | | |
|---|---|---|
| 3,760,812 A | 9/1973 | Timm et al. |
| 3,796,221 A | 3/1974 | Hagfors |
| 4,073,048 A | 2/1978 | Ditcher |
| 4,107,469 A | 8/1978 | Jenkins |
| 4,305,402 A | 12/1981 | Katims |
| 4,338,945 A | 7/1982 | Kosugi et al. |

(Continued)

FOREIGN PATENT DOCUMENTS

| | | |
|---|---|---|
| AU | 2007/233135 A1 | 10/2007 |
| AU | 2007/233205 A1 | 10/2007 |

(Continued)

OTHER PUBLICATIONS

Non-final U.S. Office Action, notification date Mar. 16, 2010 U.S. Appl. No. 11/693,499.

(Continued)

*Primary Examiner* — Carl H Layno
*Assistant Examiner* — Erica Lee
(74) *Attorney, Agent, or Firm* — Ballard Spahr LLP

(57) ABSTRACT

Disclosed herein are methods, systems, and apparatus for treating a medical condition of a patient, involving detecting a physiological cycle or cycles of the patient and applying an electrical signal to a portion of the patient's vagus nerve through an electrode at a selected point in the physiological cycle(s). The physiological cycle can be the cardiac and/or respiratory cycle. The selected point can be a point in the cardiac cycle correlated with increased afferent conduction on the vagus nerve, such as a point from about 10 msec to about 800 msec after an R-wave of the patient's ECG, optionally during inspiration by the patient. The selected point can be a point in the cardiac cycle when said applying increases heart rate variability, such as a point from about 10 msec to about 800 msec after an R-wave of the patient's ECG, optionally during expiration by the patient.

16 Claims, 10 Drawing Sheets

(56) References Cited

U.S. PATENT DOCUMENTS

| | | |
|---|---|---|
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,577,316 A | 3/1986 | Schiff |
| 4,590,946 A | 5/1986 | Loeb .............................. 604/246 |
| 4,592,339 A | 6/1986 | Kuzmak et al. |
| 4,606,349 A | 8/1986 | Livingston et al. |
| 4,608,985 A | 9/1986 | Crish et al. |
| 4,612,934 A | 9/1986 | Borkan |
| 4,625,308 A | 11/1986 | Kim et al. |
| 4,628,942 A | 12/1986 | Sweeney et al. |
| 4,649,936 A | 3/1987 | Ungar et al. |
| 4,702,254 A | 10/1987 | Zabara |
| 4,793,353 A | 12/1988 | Borkan |
| 4,867,164 A | 9/1989 | Zabara |
| 4,920,979 A | 5/1990 | Bullara |
| 4,949,721 A | 8/1990 | Toriu et al. |
| 4,977,895 A | 12/1990 | Tannenbaum |
| 4,979,511 A | 12/1990 | Terry, Jr. ....................... 128/642 |
| 5,025,807 A | 6/1991 | Zabara |
| 5,073,048 A | 12/1991 | Adachi et al. |
| 5,081,987 A | 1/1992 | Nigam |
| 5,150,508 A | 9/1992 | St. Denis |
| 5,154,172 A | 10/1992 | Terry, Jr. et al. |
| 5,179,950 A | 1/1993 | Stanislaw |
| 5,186,170 A | 2/1993 | Varrichio |
| 5,188,104 A | 2/1993 | Wernicke et al. |
| 5,205,285 A | 4/1993 | Baker, Jr. |
| 5,215,086 A | 6/1993 | Terry, Jr. et al. |
| 5,222,494 A | 6/1993 | Baker, Jr. |
| 5,231,988 A | 8/1993 | Wernicke et al. |
| 5,235,980 A | 8/1993 | Varrichio et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,354,320 A | 10/1994 | Schaldach et al. |
| 5,411,531 A | 5/1995 | Hill et al. |
| 5,411,540 A | 5/1995 | Edell et al. |
| 5,423,872 A | 6/1995 | Cigaina |
| 5,507,784 A | 4/1996 | Hill et al. |
| 5,522,862 A | 6/1996 | Testerman et al. |
| 5,522,865 A | 6/1996 | Schulman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,617 A | 2/1997 | Loeb et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,702,429 A | 12/1997 | King |
| 5,707,400 A | 1/1998 | Terry, Jr. et al. |
| 5,755,750 A | 5/1998 | Petruska et al. |
| 5,792,212 A | 8/1998 | Weijand |
| 5,800,474 A | 9/1998 | Benabid et al. |
| 5,814,092 A | 9/1998 | King |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,928,272 A * | 7/1999 | Adkins et al. .................... 607/45 |
| 5,941,906 A | 8/1999 | Barreras, Sr. et al. |
| 5,995,868 A | 11/1999 | Osorio et al. |
| 6,002,966 A | 12/1999 | Loeb et al. |
| 6,016,449 A | 1/2000 | Fischell et al. |
| 6,041,258 A | 3/2000 | Cigaina et al. |
| 6,073,048 A * | 6/2000 | Kieval et al. .................... 607/17 |
| 6,083,249 A | 7/2000 | Familoni |
| 6,101,412 A | 8/2000 | Duhaylongsod |
| 6,104,955 A | 8/2000 | Bourgeois |
| 6,104,956 A | 8/2000 | Naritoku et al. |
| 6,104,959 A | 8/2000 | Spertell |
| 6,115,628 A | 9/2000 | Stadler et al. |
| 6,132,361 A | 10/2000 | Epstein et al. |
| 6,141,590 A * | 10/2000 | Renirie et al. .................... 607/20 |
| 6,161,044 A | 12/2000 | Silverstone |
| 6,167,311 A | 12/2000 | Rezai |
| 6,175,764 B1 | 1/2001 | Loeb et al. |
| 6,188,929 B1 | 2/2001 | Giordano |
| 6,219,580 B1 | 4/2001 | Faltys et al. |
| 6,221,908 B1 | 4/2001 | Kilgard et al. |
| 6,238,423 B1 | 5/2001 | Bardy |
| 6,249,704 B1 | 6/2001 | Maltan et al. |
| 6,253,109 B1 | 6/2001 | Gielen |
| 6,266,564 B1 | 7/2001 | Hill et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,308,102 B1 | 10/2001 | Sieracki et al. |
| 6,324,421 B1 | 11/2001 | Stadler et al. |
| 6,327,503 B1 | 12/2001 | Familoni |
| 6,339,725 B1 | 1/2002 | Naritoku et al. |
| 6,341,236 B1 | 1/2002 | Osorio et al. |
| 6,353,762 B1 | 3/2002 | Baudino et al. |
| 6,356,788 B2 | 3/2002 | Boveja |
| 6,358,203 B2 | 3/2002 | Bardy |
| 6,366,813 B1 | 4/2002 | DiLorenzo |
| 6,366,814 B1 | 4/2002 | Boveja |
| 6,374,140 B1 | 4/2002 | Rise |
| 6,381,493 B1 | 4/2002 | Stadler et al. |
| 6,381,496 B1 | 4/2002 | Meadows et al. |
| 6,381,499 B1 | 4/2002 | Taylor et al. |
| 6,418,344 B1 | 7/2002 | Rezai et al. |
| 6,425,852 B1 | 7/2002 | Epstein et al. |
| 6,438,423 B1 | 8/2002 | Rezai et al. |
| 6,449,512 B1 | 9/2002 | Boveja |
| 6,453,199 B1 | 9/2002 | Kobozev |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,417 B1 | 11/2002 | Levine |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,487,446 B1 | 11/2002 | Hill et al. |
| 6,505,074 B2 | 1/2003 | Boveja et al. |
| 6,522,928 B2 | 2/2003 | Whitehurst et al. |
| 6,532,388 B1 | 3/2003 | Hill et al. |
| 6,549,804 B1 | 4/2003 | Osorio et al. |
| 6,556,868 B2 | 4/2003 | Naritoku et al. |
| 6,564,102 B1 | 5/2003 | Boveja |
| 6,565,503 B2 | 5/2003 | Leysieffer et al. |
| 6,579,280 B1 | 6/2003 | Kovach et al. |
| 6,587,719 B1 | 7/2003 | Barrett et al. |
| 6,587,724 B2 | 7/2003 | Mann |
| 6,587,726 B2 | 7/2003 | Lurie et al. |
| 6,587,727 B2 | 7/2003 | Osorio et al. |
| 6,591,138 B1 | 7/2003 | Fischell et al. |
| 6,594,524 B2 | 7/2003 | Esteller et al. |
| 6,600,953 B2 | 7/2003 | Flesler et al. |
| 6,609,025 B2 | 8/2003 | Barrett et al. |
| 6,609,030 B1 | 8/2003 | Rezai et al. |
| 6,609,031 B1 | 8/2003 | Law et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |

(56) References Cited

U.S. PATENT DOCUMENTS

| | | |
|---|---|---|
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,631,293 B2 | 10/2003 | Lyden |
| 6,656,125 B2 | 12/2003 | Misczynski et al. |
| 6,656,960 B2 | 12/2003 | Puskas |
| 6,662,053 B2 | 12/2003 | Borkan |
| 6,668,191 B1 | 12/2003 | Boveja |
| 6,671,547 B2 | 12/2003 | Lyster et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,690,973 B2 | 2/2004 | Hill et al. |
| 6,690,974 B2 | 2/2004 | Archer et al. |
| 6,708,064 B2 | 3/2004 | Rezai |
| 6,721,603 B2 | 4/2004 | Zabara et al. |
| 6,731,979 B2 | 5/2004 | MacDonald |
| 6,731,986 B2 | 5/2004 | Mann |
| 6,737,875 B2 | 5/2004 | Davis et al. |
| 6,754,530 B2 | 6/2004 | Bakels et al. |
| 6,754,536 B2 | 6/2004 | Swoyer et al. |
| 6,760,626 B1 | 7/2004 | Boveja |
| 6,764,498 B2 | 7/2004 | Mische |
| 6,768,969 B1 | 7/2004 | Nikitin et al. |
| 6,775,573 B2 | 8/2004 | Schuler et al. |
| 6,788,975 B1 | 9/2004 | Whitehurst et al. |
| 6,793,670 B2 | 9/2004 | Osorio et al. |
| 6,819,956 B2 | 11/2004 | DiLorenzo |
| 6,825,767 B2 | 11/2004 | Humbard |
| 6,826,428 B1 | 11/2004 | Chen et al. |
| 6,832,114 B1 | 12/2004 | Whitehurst et al. |
| 6,843,870 B1 | 1/2005 | Bluger |
| 6,853,862 B1 | 2/2005 | Marchal et al. |
| 6,885,888 B2 | 4/2005 | Rezai |
| 6,895,278 B1 | 5/2005 | Gordon |
| 6,900,421 B2 | 5/2005 | Varma |
| 6,901,292 B2 | 5/2005 | Hrdlicka et al. |
| 6,901,293 B2 | 5/2005 | Rogers et al. |
| 6,904,390 B2 | 6/2005 | Nikitin et al. |
| 6,907,295 B2 | 6/2005 | Gross et al. |
| 6,920,357 B2 | 7/2005 | Osorio et al. |
| 6,934,580 B1 | 8/2005 | Osorio et al. |
| 6,940,255 B2 | 9/2005 | Loch |
| 6,944,501 B1 | 9/2005 | Pless |
| 6,949,929 B2 | 9/2005 | Gray et al. |
| 6,958,705 B2 | 10/2005 | Lebel et al. |
| 6,961,618 B2 | 11/2005 | Osorio et al. |
| 7,006,859 B1 | 2/2006 | Osorio et al. |
| 7,006,872 B2 | 2/2006 | Gielen et al. |
| 7,050,856 B2 | 5/2006 | Stypulkowski |
| 7,052,983 B2 | 5/2006 | Bluger ............ 438/607 |
| 7,054,686 B2 | 5/2006 | MacDonald |
| 7,076,307 B2 | 7/2006 | Boveja et al. |
| 7,085,605 B2 | 8/2006 | Bluger et al. |
| 7,091,231 B2 | 8/2006 | Misczynski .............. 514/381 |
| 7,107,097 B2 | 9/2006 | Stern et al. |
| 7,142,923 B2 | 11/2006 | North et al. |
| 7,146,217 B2 | 12/2006 | Firlik et al. |
| 7,149,574 B2 | 12/2006 | Yun et al. |
| 7,164,941 B2 | 1/2007 | Misczynski et al. |
| 7,167,750 B2 | 1/2007 | Knudson et al. |
| 7,177,678 B1 | 2/2007 | Osorio et al. |
| 7,184,837 B2 | 2/2007 | Goetz |
| 7,188,053 B2 | 3/2007 | Nikitin et al. |
| 7,191,012 B2 | 3/2007 | Boveja et al. |
| 7,204,833 B1 | 4/2007 | Osorio et al. |
| 7,209,787 B2 | 4/2007 | DiLorenzo |
| 7,209,790 B2 | 4/2007 | Thompson et al. |
| 7,231,254 B2 | 6/2007 | DiLorenzo |
| 7,236,822 B2 | 6/2007 | Dobak, III |
| 7,236,830 B2 | 6/2007 | Gliner |
| 7,236,831 B2 | 6/2007 | Firlik et al. |
| 7,239,912 B2 | 7/2007 | Dobak, III |
| 7,239,926 B2 | 7/2007 | Goetz |
| 7,242,983 B2 | 7/2007 | Frei et al. |
| 7,242,984 B2 | 7/2007 | DiLorenzo |
| 7,249,281 B2 | 7/2007 | Shirley et al. |
| 7,252,090 B2 | 8/2007 | Goetz |
| 7,254,439 B2 | 8/2007 | Misczynski et al. |
| 7,263,405 B2 | 8/2007 | Boveja et al. |
| 7,277,758 B2 | 10/2007 | DiLorenzo |
| 7,277,761 B2 | 10/2007 | Shelchuk ............ 607/62 |
| 7,289,545 B2 | 10/2007 | Barrett ............ 372/34 |
| 7,289,844 B2 | 10/2007 | Misczynski et al. |
| 7,292,890 B2 | 11/2007 | Whitehurst et al. |
| 7,299,091 B2 | 11/2007 | Barrett et al. |
| 7,321,793 B2 | 1/2008 | Ben Ezra et al. |
| 7,340,302 B1 | 3/2008 | Falkenberg et al. |
| 7,340,306 B2 | 3/2008 | Barrett et al. |
| 7,346,395 B2 | 3/2008 | Lozano et al. |
| 7,352,285 B2 | 4/2008 | Deno ............ 640/572.1 |
| 7,363,076 B2 | 4/2008 | Yun et al. |
| 7,369,897 B2 | 5/2008 | Boveja et al. |
| 7,377,930 B2 | 5/2008 | Loughran |
| 7,395,117 B2 | 7/2008 | Mazar et al. |
| 7,418,292 B2 | 8/2008 | Shafer |
| 7,422,255 B2 | 9/2008 | Hess ............ 294/74 |
| 7,422,555 B2 | 9/2008 | Zabara |
| 7,437,196 B2 | 10/2008 | Wyler ............ 607/48 |
| 7,444,183 B2 | 10/2008 | Knudson et al. |
| 7,444,184 B2 | 10/2008 | Boveja et al. |
| 7,454,245 B2 | 11/2008 | Armstrong et al. |
| 7,454,251 B2 | 11/2008 | Rezai et al. |
| 7,454,359 B2 | 11/2008 | Rosenfeld et al. |
| 7,483,743 B2 | 1/2009 | Mann et al. |
| 7,483,747 B2 | 1/2009 | Gliner ............ 607/45 |
| 7,485,095 B2 | 2/2009 | Shusterman |
| 7,493,168 B2 | 2/2009 | Rezai |
| 7,496,409 B2 | 2/2009 | Greenhut et al. |
| 7,509,170 B2 | 3/2009 | Zhang ............ 600/512 |
| 7,512,438 B2 | 3/2009 | Fischell et al. |
| 7,519,430 B2 | 4/2009 | Von Arx et al. |
| 7,532,938 B2 | 5/2009 | Machado et al. |
| 7,541,191 B2 | 6/2009 | Machado ............ 436/70 |
| 7,542,800 B2 | 6/2009 | Libbus et al. |
| 7,547,284 B2 | 6/2009 | Brainard, II |
| 7,551,958 B2 | 6/2009 | Libbus ............ 607/2 |
| 7,561,921 B2 | 7/2009 | Phillips et al. |
| 7,565,199 B2 | 7/2009 | Sheffield et al. |
| 7,565,200 B2 | 7/2009 | Wyler et al. |
| 7,577,481 B2 | 8/2009 | Firlik ............ 607/45 |
| 7,596,413 B2 | 9/2009 | Libbus et al. |
| 7,601,115 B2 | 10/2009 | Riehl |
| 7,603,174 B2 | 10/2009 | De Ridder |
| 7,606,622 B2 | 10/2009 | Reeve |
| 7,610,083 B2 | 10/2009 | Drew et al. |
| 7,613,515 B2 | 11/2009 | Knudson et al. |
| 7,617,002 B2 | 11/2009 | Goetz |
| 7,620,455 B2 | 11/2009 | Maschino |
| 7,620,456 B2 | 11/2009 | Gliner ............ 607/45 |
| 7,623,926 B2 | 11/2009 | Rossing ............ 607/44 |
| 7,623,927 B2 | 11/2009 | Rezai |
| 7,623,928 B2 | 11/2009 | DiLorenzo |
| 7,624,293 B2 | 11/2009 | Osorio et al. |
| 7,630,757 B2 | 12/2009 | Dorfmeister et al. |
| 7,630,773 B2 | 12/2009 | Seeberger et al. |
| 7,634,317 B2 | 12/2009 | Ben-David et al. |
| 7,640,063 B2 | 12/2009 | Rezai et al. |
| 7,661,933 B2 | 2/2010 | Brockway ............ 417/413.1 |
| 7,672,730 B2 | 3/2010 | Firlik et al. |
| 7,672,733 B2 | 3/2010 | Zhou et al. |
| 7,676,263 B2 | 3/2010 | Harris et al. |
| 7,684,866 B2 | 3/2010 | Fowler et al. |
| 7,685,005 B2 | 3/2010 | Riff et al. |
| 7,689,276 B2 | 3/2010 | Dobak |
| 7,697,991 B2 | 4/2010 | Machado ............ 607/45 |
| 7,697,993 B2 | 4/2010 | Gilkerson et al. |
| 7,706,866 B2 | 4/2010 | Zhang et al. |
| 7,715,919 B2 | 5/2010 | Osorio et al. |
| 7,715,924 B2 | 5/2010 | Rezai et al. |
| 7,725,196 B2 | 5/2010 | Machado et al. |
| 7,729,773 B2 | 6/2010 | Sloan |

(56) References Cited

U.S. PATENT DOCUMENTS

| | | |
|---|---|---|
| 7,742,820 B2 | 6/2010 | Wyler .............. 607/49 |
| 7,747,325 B2 | 6/2010 | Dilorenzo |
| 7,747,551 B2 | 6/2010 | Snyder |
| 7,756,584 B2 | 7/2010 | Sheffield et al. |
| 7,761,145 B2 | 7/2010 | Virag et al. |
| 7,764,988 B2 | 7/2010 | Drew et al. |
| 7,769,465 B2 | 8/2010 | Matos |
| 7,778,704 B2 | 8/2010 | Rezai |
| 7,778,711 B2 | 8/2010 | Ben-David et al. |
| 7,783,349 B2 | 8/2010 | Libbus et al. |
| 7,801,611 B2 | 9/2010 | Persen et al. |
| 7,805,199 B2 | 9/2010 | KenKnight .............. 607/60 |
| 7,831,301 B2 | 11/2010 | Webb et al. |
| 7,831,305 B2 | 11/2010 | Gliner |
| 7,831,308 B2 | 11/2010 | Rezai et al. |
| 7,833,174 B2 | 11/2010 | Rezai et al. |
| 7,835,796 B2 | 11/2010 | Maschino et al. |
| 7,844,334 B2 | 11/2010 | Maile et al. |
| 7,844,338 B2 | 11/2010 | Knudson et al. |
| 7,853,329 B2 | 12/2010 | DiLorenzo |
| 7,856,264 B2 | 12/2010 | Firlik et al. |
| 7,856,272 B2 | 12/2010 | Nikitin et al. |
| 7,885,709 B2 | 2/2011 | Ben-David .............. 607/2 |
| 7,889,069 B2 | 2/2011 | Fifolt .............. 340/539.12 |
| 7,890,159 B2 | 2/2011 | Zhang et al. |
| 7,890,185 B2 | 2/2011 | Cohen et al. |
| 7,899,540 B2 | 3/2011 | Maschino et al. |
| 7,904,161 B2 | 3/2011 | Osypka |
| 7,908,009 B2 | 3/2011 | Wyler .............. 607/48 |
| 7,912,537 B2 | 3/2011 | Lee et al. |
| 7,917,206 B2 | 3/2011 | Frei et al. |
| 7,917,225 B2 | 3/2011 | Wyler .............. 607/45 |
| 7,930,035 B2 | 4/2011 | DiLorenzo |
| 7,933,646 B2 | 4/2011 | Frei et al. |
| 7,945,316 B2 | 5/2011 | Giftakis et al. |
| 7,945,333 B2 | 5/2011 | Jacobson |
| 7,949,401 B2 | 5/2011 | Fowler et al. |
| 7,949,404 B2 | 5/2011 | Hill |
| 7,962,218 B2 | 6/2011 | Balzer et al. |
| 7,962,220 B2 | 6/2011 | Kolafa .............. 607/46 |
| 7,974,693 B2 | 7/2011 | Ben-David et al. |
| 7,979,137 B2 | 7/2011 | Tracey et al. |
| 7,983,759 B2 | 7/2011 | Stahmann et al. |
| 7,986,997 B2 | 7/2011 | Elsner et al. |
| 7,991,625 B2 | 8/2011 | Rosenfeld .............. 705/2 |
| 8,014,865 B2 | 9/2011 | Najafi .............. 607/23 |
| 8,036,736 B2 | 10/2011 | Snyder et al. |
| 8,041,419 B2 | 10/2011 | Giftakis et al. |
| 8,046,069 B2 | 10/2011 | Kramer et al. |
| 8,046,075 B2 | 10/2011 | Rezai |
| 8,050,767 B2 | 11/2011 | Sheffield et al. |
| 8,065,011 B2 | 11/2011 | Echauz et al. |
| 8,065,012 B2 | 11/2011 | Firlik et al. |
| 8,068,918 B2 | 11/2011 | Vallapureddy et al. |
| 8,096,954 B2 | 1/2012 | Stahmann et al. |
| 8,108,033 B2 | 1/2012 | Drew et al. |
| 8,108,038 B2 | 1/2012 | Giftakis .............. 600/513 |
| 8,108,046 B2 | 1/2012 | Giftakis et al. |
| 8,108,048 B2 | 1/2012 | Masoud |
| 8,111,150 B2 | 2/2012 | Miller et al. |
| 8,112,148 B2 | 2/2012 | Giftakis et al. |
| 8,112,153 B2 | 2/2012 | Giftakis et al. |
| 8,123,668 B2 | 2/2012 | Annest et al. |
| 8,126,529 B2 | 2/2012 | Johnson et al. |
| 8,126,568 B2 | 2/2012 | Gliner |
| 8,137,269 B2 | 3/2012 | Sheikhzadeh-Nadjar et al. |
| 8,150,508 B2 | 4/2012 | Craig .............. 607/2 |
| 8,155,742 B2 | 4/2012 | Ball et al. |
| 8,165,682 B2 | 4/2012 | Gopalsami .............. 607/45 |
| 8,170,668 B2 | 5/2012 | Ettori et al. |
| 8,175,705 B2 | 5/2012 | Libbus |
| 8,187,181 B2 | 5/2012 | Osorio et al. |
| 8,209,009 B2 | 6/2012 | Giftakis et al. |
| 8,209,018 B2 | 6/2012 | Osorio et al. |
| 8,211,033 B2 | 7/2012 | Siejko et al. |
| 8,214,043 B2 | 7/2012 | Matos |
| 8,219,188 B2 | 7/2012 | Craig |
| 8,280,505 B2 | 10/2012 | Craig |
| 2001/0034541 A1 | 10/2001 | Lyden |
| 2001/0037220 A1 | 11/2001 | Merry et al. |
| 2002/0052539 A1 | 5/2002 | Haller et al. |
| 2002/0065509 A1 | 5/2002 | Lebel et al. |
| 2002/0072782 A1 | 6/2002 | Osorio et al. |
| 2002/0082480 A1 | 6/2002 | Riff et al. |
| 2002/0099412 A1 | 7/2002 | Fischell et al. |
| 2002/0099417 A1 | 7/2002 | Naritoku et al. |
| 2002/0116030 A1 | 8/2002 | Rezai |
| 2002/0120310 A1 | 8/2002 | Linden et al. |
| 2002/0133204 A1 | 9/2002 | Hrdlicka |
| 2002/0143368 A1 | 10/2002 | Bakels et al. |
| 2002/0151939 A1 | 10/2002 | Rezai |
| 2002/0153901 A1 | 10/2002 | Davis et al. |
| 2002/0188214 A1 | 12/2002 | Misczynski et al. |
| 2003/0028226 A1 | 2/2003 | Thompson et al. |
| 2003/0036780 A1 | 2/2003 | Barrett et al. |
| 2003/0040774 A1* | 2/2003 | Terry et al. .............. 607/2 |
| 2003/0055457 A1 | 3/2003 | MacDonald |
| 2003/0074032 A1 | 4/2003 | Gliner |
| 2003/0083716 A1 | 5/2003 | Nicolelis et al. |
| 2003/0088274 A1 | 5/2003 | Gliner et al. |
| 2003/0095648 A1 | 5/2003 | Kaib et al. |
| 2003/0097161 A1 | 5/2003 | Firlik et al. |
| 2003/0109903 A1 | 6/2003 | Berrang et al. |
| 2003/0125786 A1 | 7/2003 | Gliner et al. |
| 2003/0130706 A1 | 7/2003 | Sheffield et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0181959 A1 | 9/2003 | Dobak |
| 2003/0195574 A1 | 10/2003 | Osorio et al. |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0015205 A1 | 1/2004 | Whitehurst et al. |
| 2004/0024428 A1 | 2/2004 | Barrett et al. |
| 2004/0036377 A1 | 2/2004 | Mezinis |
| 2004/0039424 A1 | 2/2004 | Merritt et al. |
| 2004/0039427 A1 | 2/2004 | Barrett et al. |
| 2004/0088024 A1 | 5/2004 | Firlik et al. |
| 2004/0111139 A1 | 6/2004 | McCreery |
| 2004/0112894 A1 | 6/2004 | Varma |
| 2004/0122484 A1 | 6/2004 | Hatlestad et al. |
| 2004/0122485 A1 | 6/2004 | Stahmann et al. |
| 2004/0122489 A1 | 6/2004 | Mazar et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138518 A1 | 7/2004 | Rise et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0147992 A1 | 7/2004 | Bluger et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0167583 A1 | 8/2004 | Knudson et al. |
| 2004/0167587 A1 | 8/2004 | Thompson |
| 2004/0172085 A1 | 9/2004 | Knudson et al. |
| 2004/0172088 A1 | 9/2004 | Knudson et al. |
| 2004/0172089 A1 | 9/2004 | Whitehurst et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0193231 A1 | 9/2004 | David et al. |
| 2004/0199146 A1 | 10/2004 | Rogers et al. |
| 2004/0199187 A1 | 10/2004 | Loughran |
| 2004/0199210 A1 | 10/2004 | Shelchuk |
| 2004/0199212 A1 | 10/2004 | Fischell et al. |

(56) References Cited

U.S. PATENT DOCUMENTS

| | | |
|---|---|---|
| 2004/0210270 A1 | 10/2004 | Erickson |
| 2004/0210274 A1 | 10/2004 | Bauhahn et al. |
| 2004/0249302 A1 | 12/2004 | Donoghue et al. |
| 2004/0249416 A1 | 12/2004 | Yun et al. |
| 2004/0254612 A1 | 12/2004 | Ezra et al. |
| 2004/0254616 A1* | 12/2004 | Rossing et al. ............... 607/42 |
| 2004/0260346 A1 | 12/2004 | Overall et al. |
| 2004/0263172 A1 | 12/2004 | Gray et al. |
| 2005/0004615 A1 | 1/2005 | Sanders |
| 2005/0004621 A1 | 1/2005 | Boveja et al. |
| 2005/0010262 A1 | 1/2005 | Rezai et al. |
| 2005/0015128 A1 | 1/2005 | Rezai et al. |
| 2005/0016657 A1 | 1/2005 | Bluger |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0028026 A1 | 2/2005 | Shirley et al. |
| 2005/0033378 A1 | 2/2005 | Sheffield et al. |
| 2005/0033379 A1 | 2/2005 | Lozano et al. |
| 2005/0038326 A1 | 2/2005 | Mathur |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0060007 A1 | 3/2005 | Goetz |
| 2005/0060008 A1 | 3/2005 | Goetz |
| 2005/0060009 A1 | 3/2005 | Goetz |
| 2005/0060010 A1 | 3/2005 | Goetz |
| 2005/0065553 A1 | 3/2005 | Ben Ezra et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0075681 A1 | 4/2005 | Rezai et al. |
| 2005/0075691 A1 | 4/2005 | Phillips et al. |
| 2005/0075701 A1 | 4/2005 | Shafer |
| 2005/0075702 A1 | 4/2005 | Shafer |
| 2005/0088145 A1 | 4/2005 | Loch |
| 2005/0101873 A1 | 5/2005 | Misczynski et al. |
| 2005/0102002 A1 | 5/2005 | Salo et al. |
| 2005/0107753 A1 | 5/2005 | Rezai et al. |
| 2005/0107842 A1 | 5/2005 | Rezai ......................... 604/891.1 |
| 2005/0107858 A1 | 5/2005 | Bluger |
| 2005/0113705 A1 | 5/2005 | Fischell et al. |
| 2005/0113744 A1 | 5/2005 | Donoghue et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0131506 A1 | 6/2005 | Rezai et al. |
| 2005/0137480 A1 | 6/2005 | Alt et al. |
| 2005/0143781 A1 | 6/2005 | Carbunaru et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154435 A1 | 7/2005 | Stern et al. |
| 2005/0159789 A1 | 7/2005 | Brockway et al. |
| 2005/0161052 A1 | 7/2005 | Rezai et al. |
| 2005/0165458 A1 | 7/2005 | Boveja et al. |
| 2005/0177192 A1 | 8/2005 | Rezai et al. |
| 2005/0177200 A1 | 8/2005 | George et al. |
| 2005/0177206 A1 | 8/2005 | North et al. |
| 2005/0182389 A1 | 8/2005 | LaPorte et al. |
| 2005/0187590 A1 | 8/2005 | Boveja et al. |
| 2005/0187593 A1 | 8/2005 | Housworth et al. |
| 2005/0187796 A1 | 8/2005 | Rosenfeld et al. |
| 2005/0192644 A1 | 9/2005 | Boveja et al. |
| 2005/0197590 A1 | 9/2005 | Osorio et al. |
| 2005/0197675 A1 | 9/2005 | David et al. |
| 2005/0222631 A1 | 10/2005 | Dalal et al. |
| 2005/0228693 A1 | 10/2005 | Webb et al. |
| 2005/0240246 A1 | 10/2005 | Lee et al. |
| 2005/0245944 A1 | 11/2005 | Rezai |
| 2005/0245971 A1 | 11/2005 | Brockway et al. |
| 2005/0245990 A1 | 11/2005 | Roberson |
| 2005/0251220 A1 | 11/2005 | Barrett et al. |
| 2005/0251222 A1 | 11/2005 | Barrett et al. |
| 2005/0261542 A1 | 11/2005 | Riehl |
| 2005/0267542 A1 | 12/2005 | David et al. |
| 2005/0267550 A1 | 12/2005 | Hess et al. |
| 2005/0272280 A1 | 12/2005 | Osypka |
| 2005/0277872 A1 | 12/2005 | Colby, Jr. et al. |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0283208 A1 | 12/2005 | Von Arx et al. |
| 2005/0288600 A1 | 12/2005 | Zhang et al. |
| 2005/0288736 A1 | 12/2005 | Persen et al. |
| 2005/0288760 A1 | 12/2005 | Machado et al. |
| 2006/0009815 A1 | 1/2006 | Boveja |
| 2006/0015153 A1* | 1/2006 | Gliner et al. ................... 607/45 |
| 2006/0020292 A1 | 1/2006 | Goetz et al. |
| 2006/0020491 A1 | 1/2006 | Mongeon et al. |
| 2006/0041222 A1 | 2/2006 | Dewing et al. |
| 2006/0041223 A1 | 2/2006 | Dewing et al. |
| 2006/0041287 A1 | 2/2006 | Dewing et al. |
| 2006/0047205 A1 | 3/2006 | Ludomirsky et al. |
| 2006/0052843 A1 | 3/2006 | Elsner et al. |
| 2006/0058597 A1 | 3/2006 | Machado et al. |
| 2006/0064133 A1 | 3/2006 | Von Arx et al. |
| 2006/0064134 A1 | 3/2006 | Mazar et al. |
| 2006/0064143 A1 | 3/2006 | Von Arx et al. |
| 2006/0069322 A1 | 3/2006 | Zhang et al. |
| 2006/0074450 A1 | 4/2006 | Boveja |
| 2006/0079936 A1 | 4/2006 | Boveja |
| 2006/0079942 A1 | 4/2006 | Deno et al. |
| 2006/0079945 A1 | 4/2006 | Libbus |
| 2006/0085046 A1 | 4/2006 | Rezai et al. |
| 2006/0094971 A1 | 5/2006 | Drew |
| 2006/0095081 A1 | 5/2006 | Zhou et al. |
| 2006/0095090 A1 | 5/2006 | De Ridder |
| 2006/0100667 A1 | 5/2006 | Machado et al. |
| 2006/0100668 A1* | 5/2006 | Ben-David et al. ............... 607/2 |
| 2006/0100671 A1 | 5/2006 | Ridder |
| 2006/0106430 A1 | 5/2006 | Fowler et al. |
| 2006/0106431 A1 | 5/2006 | Wyler et al. |
| 2006/0111644 A1 | 5/2006 | Guttag et al. |
| 2006/0122525 A1 | 6/2006 | Shusterman |
| 2006/0122667 A1 | 6/2006 | Chavan et al. |
| 2006/0122864 A1 | 6/2006 | Gottesman et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1 | 7/2006 | Armstrong et al. |
| 2006/0173493 A1 | 8/2006 | Armstrong et al. |
| 2006/0173494 A1 | 8/2006 | Armstrong et al. |
| 2006/0173522 A1 | 8/2006 | Osorio |
| 2006/0190056 A1 | 8/2006 | Fowler et al. |
| 2006/0195155 A1 | 8/2006 | Firlik et al. |
| 2006/0195163 A1 | 8/2006 | KenKnight et al. |
| 2006/0200206 A1 | 9/2006 | Firlik et al. |
| 2006/0200208 A1 | 9/2006 | Terry, Jr. et al. |
| 2006/0212091 A1 | 9/2006 | Lozano et al. |
| 2006/0217780 A1 | 9/2006 | Gliner et al. |
| 2006/0220839 A1 | 10/2006 | Fifolt et al. |
| 2006/0224067 A1 | 10/2006 | Giftakis et al. |
| 2006/0224188 A1 | 10/2006 | Libbus et al. |
| 2006/0224191 A1 | 10/2006 | DiLorenzo |
| 2006/0241697 A1 | 10/2006 | Libbus et al. |
| 2006/0241725 A1 | 10/2006 | Libbus et al. |

(56) References Cited

U.S. PATENT DOCUMENTS

| | | |
|---|---|---|
| 2006/0247719 A1 | 11/2006 | Maschino et al. |
| 2006/0247722 A1 | 11/2006 | Maschino et al. |
| 2006/0253164 A1 | 11/2006 | Zhang et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0264730 A1 | 11/2006 | Stivoric et al. |
| 2006/0265018 A1 | 11/2006 | Smith et al. |
| 2006/0271108 A1 | 11/2006 | Libbus et al. |
| 2006/0271409 A1 | 11/2006 | Rosenfeld et al. |
| 2006/0293720 A1 | 12/2006 | DiLorenzo |
| 2006/0293721 A1 | 12/2006 | Tarver et al. |
| 2007/0021786 A1 | 1/2007 | Parnis et al. |
| 2007/0027486 A1 | 2/2007 | Armstrong et al. |
| 2007/0032734 A1 | 2/2007 | Najafi et al. |
| 2007/0032834 A1 | 2/2007 | Gliner et al. |
| 2007/0038262 A1 | 2/2007 | Kieval et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073346 A1 | 3/2007 | Corbucci et al. |
| 2007/0073355 A1 | 3/2007 | DiLorenzo |
| 2007/0078491 A1 | 4/2007 | Siejko et al. |
| 2007/0088403 A1 | 4/2007 | Wyler et al. |
| 2007/0088404 A1 | 4/2007 | Wyler et al. |
| 2007/0088405 A1 | 4/2007 | Jacobson et al. |
| 2007/0100278 A1 | 5/2007 | Frei et al. |
| 2007/0100397 A1 | 5/2007 | Seeberger et al. |
| 2007/0100398 A1 | 5/2007 | Sloan |
| 2007/0112393 A1 | 5/2007 | Gliner et al. |
| 2007/0123946 A1 | 5/2007 | Masoud |
| 2007/0135855 A1 | 6/2007 | Foshee et al. |
| 2007/0142862 A1 | 6/2007 | DiLorenzo |
| 2007/0142873 A1 | 6/2007 | Esteller et al. |
| 2007/0149952 A1 | 6/2007 | Bland et al. |
| 2007/0150011 A1 | 6/2007 | Meyer et al. |
| 2007/0150014 A1 | 6/2007 | Kramer et al. |
| 2007/0150024 A1 | 6/2007 | Leyde et al. |
| 2007/0150025 A1 | 6/2007 | DiLorenzo et al. |
| 2007/0156179 A1 | 7/2007 | S.E. |
| 2007/0156450 A1 | 7/2007 | Roehm et al. |
| 2007/0156626 A1 | 7/2007 | Roehm et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0179534 A1 | 8/2007 | Firlik et al. |
| 2007/0179558 A1 | 8/2007 | Gliner et al. |
| 2007/0179584 A1 | 8/2007 | Gliner |
| 2007/0203548 A1 | 8/2007 | Pawelzik et al. |
| 2007/0208212 A1 | 9/2007 | DiLorenzo |
| 2007/0208390 A1 | 9/2007 | Von Arx et al. |
| 2007/0213785 A1 | 9/2007 | Osorio et al. |
| 2007/0233192 A1 | 10/2007 | Craig |
| 2007/0233193 A1 | 10/2007 | Craig ............................. 607/45 |
| 2007/0238939 A1 | 10/2007 | Giftakis et al. |
| 2007/0239210 A1 | 10/2007 | Libbus et al. |
| 2007/0239211 A1 | 10/2007 | Lorincz et al. |
| 2007/0239220 A1 | 10/2007 | Greenhut et al. |
| 2007/0244407 A1 | 10/2007 | Osorio |
| 2007/0249953 A1 | 10/2007 | Osorio et al. |
| 2007/0249954 A1 | 10/2007 | Virag et al. |
| 2007/0250130 A1 | 10/2007 | Ball et al. |
| 2007/0250145 A1 | 10/2007 | Kraus et al. |
| 2007/0255147 A1 | 11/2007 | Drew et al. |
| 2007/0255155 A1 | 11/2007 | Drew et al. |
| 2007/0255330 A1 | 11/2007 | Lee et al. |
| 2007/0255337 A1 | 11/2007 | Lu |
| 2007/0255374 A1 | 11/2007 | Kolafa et al. |
| 2007/0260147 A1 | 11/2007 | Giftakis et al. |
| 2007/0260289 A1 | 11/2007 | Giftakis et al. |
| 2007/0265489 A1 | 11/2007 | Fowler et al. |
| 2007/0265508 A1 | 11/2007 | Sheikhzadeh-Nadjar et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2007/0287931 A1 | 12/2007 | DiLorenzo |
| 2007/0288072 A1 | 12/2007 | Pascual-Leone et al. |
| 2007/0299349 A1 | 12/2007 | Alt et al. |
| 2007/0299473 A1 | 12/2007 | Matos |
| 2007/0299480 A1 | 12/2007 | Hill |
| 2008/0015651 A1 | 1/2008 | Ettori et al. |
| 2008/0015652 A1 | 1/2008 | Maile et al. |
| 2008/0021332 A1 | 1/2008 | Brainard, III |
| 2008/0021341 A1 | 1/2008 | Harris et al. |
| 2008/0021517 A1 | 1/2008 | Dietrich |
| 2008/0021520 A1 | 1/2008 | Dietrich |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0033503 A1 | 2/2008 | Fowler et al. |
| 2008/0033508 A1 | 2/2008 | Frei et al. |
| 2008/0039895 A1 | 2/2008 | Fowler et al. |
| 2008/0046035 A1 | 2/2008 | Fowler et al. |
| 2008/0046037 A1 | 2/2008 | Haubrich et al. |
| 2008/0046038 A1 | 2/2008 | Hill et al. |
| 2008/0051852 A1 | 2/2008 | Dietrich et al. |
| 2008/0058884 A1 | 3/2008 | Matos |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0081962 A1 | 4/2008 | Miller et al. |
| 2008/0082132 A1 | 4/2008 | Annest et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146890 A1 | 6/2008 | LeBoeuf et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0183245 A1 | 7/2008 | Van Oort et al. |
| 2008/0195175 A1 | 8/2008 | Balzer et al. |
| 2008/0200925 A1 | 8/2008 | Johnson |
| 2008/0208013 A1 | 8/2008 | Zhang et al. |
| 2008/0208074 A1 | 8/2008 | Snyder et al. |
| 2008/0208285 A1 | 8/2008 | Fowler et al. |
| 2008/0208291 A1 | 8/2008 | Leyde et al. |
| 2008/0208781 A1 | 8/2008 | Snyder |
| 2008/0215112 A1 | 9/2008 | Firlik et al. |
| 2008/0215114 A1 | 9/2008 | Stuerzinger et al. |
| 2008/0221644 A1 | 9/2008 | Vallapureddy et al. |
| 2008/0234598 A1 | 9/2008 | Snyder et al. |
| 2008/0249591 A1 | 10/2008 | Gaw et al. |
| 2008/0255582 A1 | 10/2008 | Harris |
| 2009/0054795 A1 | 2/2009 | Misczynski et al. |
| 2009/0076567 A1 | 3/2009 | Fowler et al. |
| 2009/0171405 A1 | 7/2009 | Craig ............................. 607/2 |
| 2009/0177252 A1 | 7/2009 | Craig |
| 2012/0191158 A1 | 7/2012 | Craig |

FOREIGN PATENT DOCUMENTS

| | | |
|---|---|---|
| AU | 2012202405 A1 | 5/2012 |
| AU | 2012202408 A1 | 5/2012 |
| BR | 2116 | 7/2011 |
| BR | 0709844-8 | 7/2011 |
| CA | 2339971 | 6/2004 |
| CA | 2653110 A1 | 10/2007 |
| CA | 2653112 A1 | 10/2007 |
| EP | 0402683 | 5/1990 |
| EP | 0713714 | 7/1995 |
| EP | 1070518 | 5/2000 |
| EP | 1145736 | 10/2001 |

(56) References Cited

FOREIGN PATENT DOCUMENTS

| | | |
|---|---|---|
| EP | 1304135 A2 | 4/2003 |
| EP | 1486232 | 12/2004 |
| EP | 1486232 A2 | 12/2004 |
| EP | 1595497 | 11/2005 |
| EP | 1120130 | 12/2005 |
| EP | 1634617 A1 | 3/2006 |
| EP | 1647300 | 4/2006 |
| EP | 1745818 | 1/2007 |
| EP | 2004283 A1 | 12/2008 |
| EP | 2007477 A1 | 12/2008 |
| EP | 2026874 A1 | 2/2009 |
| GB | 2026870 | 2/1980 |
| GB | 2079610 | 1/1982 |
| IL | 194407 | 9/2008 |
| IL | 194406 A | 8/2012 |
| JP | 2001-505441 | 4/2001 |
| JP | 2003-180847 | 7/2003 |
| JP | 2004-524125 | 8/2004 |
| JP | 2009/503279 A | 1/2009 |
| JP | 2009-503285 | 1/2009 |
| JP | 11-514268 | 5/2011 |
| JP | 2011-514268 A | 5/2011 |
| WO | 9301862 | 2/1993 |
| WO | 9302744 | 2/1993 |
| WO | 93/21824 A1 | 11/1993 |
| WO | 9400185 | 1/1994 |
| WO | 9400188 | 1/1994 |
| WO | WO 9417771 | 8/1994 |
| WO | WO 9825688 | 6/1998 |
| WO | 9956822 | 11/1999 |
| WO | WO 0040143 | 7/2000 |
| WO | WO 0064336 | 11/2000 |
| WO | WO 0105467 | 1/2001 |
| WO | WO 0108749 | 2/2001 |
| WO | WO 0064336 A9 | 6/2002 |
| WO | WO 03076010 | 9/2003 |
| WO | WO 03085546 | 10/2003 |
| WO | WO 2004036377 | 4/2004 |
| WO | WO 2004064918 | 8/2004 |
| WO | WO 2004069330 | 8/2004 |
| WO | WO 2004071575 | 8/2004 |
| WO | WO 2004075982 | 9/2004 |
| WO | WO 2004112894 | 12/2004 |
| WO | WO 2005007120 | 1/2005 |
| WO | WO 2005007232 | 1/2005 |
| WO | WO 2005028026 A1 | 3/2005 |
| WO | WO 2005053788 | 6/2005 |
| WO | WO 2005067599 | 7/2005 |
| WO | WO 2005101282 | 10/2005 |
| WO | WO 2006/019764 | 2/2006 |
| WO | WO 2006014760 | 2/2006 |
| WO | WO 2006019822 | 2/2006 |
| WO | WO 2006050144 | 5/2006 |
| WO | 2006118793 | 11/2006 |
| WO | WO 2006122148 | 11/2006 |
| WO | WO 2007066343 A2 | 6/2007 |
| WO | WO 2007072425 | 6/2007 |
| WO | WO 2007/115103 | 10/2007 |
| WO | WO 2007/115113 | 10/2007 |
| WO | WO 2007/115118 | 10/2007 |
| WO | WO 2007124126 | 11/2007 |
| WO | WO 2007124190 | 11/2007 |
| WO | WO 2007124192 | 11/2007 |
| WO | WO 2007142523 | 12/2007 |

OTHER PUBLICATIONS

Non-final U.S. Office Action, notification date Mar. 17, 2010, U.S. Appl. No. 12/400,893.

Bachman, D.,S. et al.; "*Effects of Vagal Volleys and Serotonin on Units of Cingulate Cortex in Monkeys*;" Brain Research, vol. 130 (1977). pp. 253-269.

Bohning, D.E., et al.; "*Feasibility of Vagus Nerve Stimulation—Synchronized Blood Oxygenation Level-Dependent Functional MRI*;" A Journal of Clinical and Laboratory Research: Investigative Radiology; vol. 36, No. 8 (Aug. 2001); pp. 470-479.

Boon, Paul, et al.; "*Programmed and Magnet-Induced Vagus Nerve Stimulation for Refractory Epilepsy*;" Journal of Clinical Neurophysiology vol. 18 No. 5; (2001); pp. 402-407.

Clark, K.B., et al.; "*Posttraining Electrical Stimulation of Vagal Afferents with Concomitant Vagal Efferent Inactivation Enhances Memory Storage Processes in the Rat*;" Neurobiology of Learning and Memory, vol. 70, 364-373 (1998) Art. No. NL983863.

Clark, K.B., et al.; "*Enhanced Recognition Memory Following Vagus Nerve Stimulation in Human Subjects*;" Nature Neuroscience, vol. 2, No. 1, (Jan. 1999) pp. 93-98.

Craig, A.D. (Bud); "*Distribution of Trigeminothalamic and Spinothalamic Lamina I Terminations in the Macaque Monkey*;" The Journal of Comparative Neurology, vol. 477, pp. 119-148 (2004).

DeGiorgo, Christopher M., et al.; "Vagus Nerve Stimulation: Analysis of Device Parameters in 154 Patients During the Long-Term XE5 Study;" *Epilepsia*, vol. 42, No. 8; pp. 1017-1020 (2001).

Devous, Michael D., et al.; "*Effects of Vagus Nerve Stimulation on Regional Cerebral Blood Flow in Treatment-Resistant Depression*;" National Institute of Mental Health—42nd Annual NCDEU Meeting: Poster Session II; Poster Abstracts, Jun. 10-13, 2002, 1 page; http://www.nimh.nih.gov/ncdeu/abstracts2002/ncdeu2019.cfm.

Dodrill, Ph.D., et al.; "*Effects of Vagal Nerve Stimulation on Cognition and Quality of Life in Epilepsy*;" Epilepsy and Behavior, vol. 2 (2001); pp. 46-53.

Fanselow, E. E., et al.; "*Reduction of Pentylenetetrazole-Induced Seizure Activity in Awake Rats by Seizure-Triggered Trigeminal Nerve Stimulation*;" The Journal of Neuroscience, vol. 20, No. 21; (Nov. 2000); pp. 8160-8168.

Fromes, G. A.et al.; "Clinical Utility of On-Demand Magnet use with Vagus Nerve Stimulation;" AES Proceedings, p. 117.

George, M.S., et al.; "*Open Trial of VNS Therapy in Severe Anxiety Disorders*;" 156th American Psychiatric Association Annual Meeting; May 17-22, 2003.

George, M.S., et al.; "*Vagus Nerve Stimulation: A New Tool for Brain Research and Therapy*;" Society of Biological Psychiatry vol. 47 (2000) pp. 287-295.

Hallowitz, R.A., et al.; "*Effects of Vagal Tolleys on Units of Intralaminar and Juxtalaminar Thalamic Nuclei in Monkeys*;" Brain Research, vol. 130 (1977), pp. 271-286.

Harry, J.D., et al.; "*Balancing Act: Noise is the Key to Restoring the Body's Sense of Equilibrium*;" IEEE Spectrum (Apr. 2005)pp. 37-41.

Henry, T.R., et al.; "Brain Blood-Flow Alterations Induced by Therapeutic Vagus Nerve Stimulation in Partial Epilepsy: I. Acute Effects at High and Low Levels of Stimulation;" *Epilepsia* vol. 39, No. 9; pp. 984-990 (1998).

Henry, MD, T.R.; "*Therapeutic Mechanisms of Vagus Nerve Stimulation*" Neurology, vol. 59 Suppl. 4 (Sep. 2002); pp. S3-S14.

King, M.D., "*Effects of Short-Term Vagus Nerve Stimulation (VNS) on FOS Expression in Rat Brain Nuclei*" 58th Annual Scientific Convention of the Society of Biological Psychiatry, (May 2003).

Klapper, M.D., et al., "*VNS Therapy Shows Potential Benefit in Patients with Migraine and Chronic Daily Headache After 3 to 6 Months of Treatment (Preliminary Results)*" 45th Annual Scientific Meeting of the American Headache Society (Jun. 2003).

Koo, B., "*EEG Changes With Vagus Nerve Stimulation*" Journal of Clinical Neurophysiology, vol. 18 No. 5 (Sep. 2001); pp. 434-441.

Labar, D., "*Vagus Nerve Stimulation for 1 Year in 269 patients on Unchanged Antiepilectic Drugs*" Seizure vol. 13, (2004) pp. 392-398.

Lockard et al., "*Feasibility and Safety of Vagal Stimulation in Monkey Model*;" Epilepsia, vol. 31 (Supp. 2) (1990), pp. S20-S26.

Liebman, K.M. et al.; "Improvement in Cognitive Function After Vagal Nerve Stimulator Implantation;" *Epilepsia*, vol. 39, Suppl. 6 (1998) 1 page.

Malow, B.A., et al.; "*Vagus Nerve Stimulation Reduces Daytime Sleepiness in Epilepsy Patients*" Neurology 57 (2001) pp. 879-884.

McClintock, P., "*Can Noise Actually Boost Brain Power*" Physics World Jul. 2002; pp. 20-21.

Mori, T., et al.; "*Noise-Induced Entrainment and Stochastic Resonance in Human Brain Waves*" Physical Review Letters vol. 88, No. 21 (2002); pp. 218101-1-218101-4.

(56) References Cited

OTHER PUBLICATIONS

Rugg-Gunn, F.J., et al.; "*Cardiac Arrhythmias in Focal Epilepsy: a Prospective Long-Term Study*" www.thelancet.com vol. 364 (2004) pp. 2212-2219.
Rutecki, P.; "Anatomical, Physiological, and Theoretical Basis for the Antiepileptic Effect of Vagus Nerve Stimulation" *Epilepsia*, vol. 31 Suppl. 2; S1-S6 (1990).
Sahin, M.; et al.; "*Improved Nerve Cuff Electrode Recordings with Subthreshold Anodic Currents*;" IEEE Transactions on Biomedical Engineering, vol. 45, No. 8 (Aug. 1998) pp. 1044-1050.
Schachter, S.C., et al.; "Progress in Epilepsy Research: Vagus Nerve Stimulation;" *Epilepsia*, vol. 39, No. 7 (1998) pp. 677-686.
Tatum, W.O., et al.; "*Ventricular Asystole During Vagus Nerve Stimulation for Epilepsy in Humans*" American Academy of Neurologgy (1999) p. 1267 (See also pp. 1117, 1166, and 1265).
Tatum, W.O., et al.; "*Vagus Nerve Stimulation and Drug Reduction*" Neurology, vol. 56, No. 4 (Feb. 2001) pp. 561-563.
Terry et al.; "*The Implantable Neurocybernetic Prosthesis System*", Pacing and Clinical Electrophysiology, vol. 14, No. 1 (Jan. 1991), pp. 86-93.
Tubbs, R.S., et al.; "*Left-Sided Vagus Nerve Stimulation Decreases Intracranial Pressure Without Resultant Bradycardia in the Pig: A Potential Therapeutic Modality for Humans*" Child's Nervous System Original Paper; Springer-Verlag 2004.
Valdez-Cruz, A., et al.; "*Chronic Stimulation of the Cat Vagus Nerve Effect on Sleep and Behavior*" Progress in Neuro-Psychopharmacology & Biological Psychiatry, vol. 26 (2002) pp. 113-118.
Vonck, K., et al. "*The Mechanism of Action of Vagus Nerve Stimulation for Refractory Epilepsy—The Current Status*", Journal of Neurophysiology, vol. 18 No. 5 (2001), pp. 394-401.
Ward, H., M.D., et al.; "*Treatment-Refractory Obsessive-Compulsive Disorder: Potential Benefit of VNS Therapy*" 23rd Annual Conference of the Anxiety Disorders Association of America (2007).
Woodbury, et al., "*Vagal Stimulation Reduces the Severity of Maximal Electroshock Seizures in Intact Rats. Use of a Cuff Electrode for Stimulating and Recording*"; Pacing and Clinical Electrophysiology, vol. 14 (Jan. 1991), pp. 94-107.
Zabara, J. "*Inhibition of Experimental Seizures in Canines by Repetivie Vagal Stimulation*" Epilepsia vol. 33, No. 6 (1992); pp. 1005-1012.
Craig, A.D. (Bud), Mechanisms of Thalamic Pain; Central Neuropathic Pain; Focus on Poststroke Pain, 2007, IASP Press, Seattle, Washington.
Craig, A.D. (Bud), Vagal Input to Lateral Area 3a in Cat Cortex; J. Neurophysiol 90, Jan. 15, 2003, 143-154; USA.
Ito, S.; Craig, A.D., Forebrain Projections of the Vagal Responsive Site in the Thalamic Parafascicular Nucleus in Monkeys; Nov. 13, 2005; Presentation 305.2, Washington D.C.
Ito, S.; Craig, A.D., Forebrain Projections from Different Portions of the Vagal Responsive Region in the Thalamic Parafascicular Nucleus in Monkeys; Oct. 15, 2006; Program 166.9/AA28, USA.
Ito, S.; Craig, A.D., Vagal-Evoked Activity in the Parafascicular Nucleus of the Primate Thalamus; J. Neurophysiol 94, May 31, 2005, 2976-2982; USA.
Restriction Requirement in U.S. Appl. No. 11/693,421, Mar. 18, 2010.
First Office Action in U.S. Appl. No. 11/693,451, Apr. 21, 2010.
Examination Report in European Patent Application No. 07 759 728.4, Mailing Date: Apr. 27, 2010.
Examination RAeport in European Patent Application No. 07 759 722.7, Mailing Date: Apr. 27, 2010.
Examination Report in European Patent Application No. 07 759 710.2, Mailing Date: Apr. 13, 2010.
Examination Report in European Patent Application 07 759 728.4, Mailing Date: Aug. 8, 2009.
Examination Report in European Patent Application 07 759 710.2, Mailing Date: Jun. 10, 2009.
Examination Report in European Patent Application 07 759 722.7, Mailing Date: Jun. 16, 2009.
Examiner's First Report in Australian Patent Application No. 2007233135, Mailing Date: Aug. 9, 2010.
Office Action in U.S. Appl. No. 11/693,421, Mailing Date: Aug. 12, 2010.
Office Action in U.S. Appl. No. 12/400,893, Mailing Date: Aug. 10, 2010.
Examination Report in Australian Patent Application No. 2007233205, Mailing Date: Aug. 9, 2010.
Final Office Action in U.S. Appl. No. 11/693,499, Mailing Date: Sep. 28, 2010.
Klabunde, R.E. "Electrocardiogram (EKG, ECG)." Cardiovascular Physiology Concepts. http://www.cvphysiology.com/Arrhythmias/A009.htm. Revised Apr. 6, 2007.
Advisory Action issued Jun. 15, 2011 for U.S. Appl. No. 11/693,499, filed Mar. 29, 2007 (Inventor—Arthur D. Craig; Applicant—Dignity Health) (pp. 1-3).
Amended Claim Set filed Dec. 22, 2008 for European Patent Application 0759722, which was filed Mar. 29, 2007 (Inventor—Arthur D. Craig Applicant—Dignity Health) (pp. 1-11).
Amendment After Non-Final Office Action filed Aug. 16, 2010 for U.S. Appl. No. 11/693,499, filed Mar. 29, 2007 (Inventor—Arthur D. Craig; Applicant—Dignity Health) (pp. 1-8).
Amendment and Response to Final Office Action filed Apr. 5, 2012 for U.S. Appl. No. 12/400,893, filed Mar. 10, 2009 (Inventor—Arthur D. Craig; Applicant—Dignity Health) (pp. 1-9).
Amendment and Response to Final Office Action filed Oct. 10, 2011 for U.S. Appl. No. 11/693,421, filed Mar. 29, 2007 (Inventor—Arthur D. Craig; Applicant—Dignity Health) (pp. 1-18).
Amendment and Response to Non-Final Office Action filed Aug. 23, 2011 for U.S. Appl. No. 12/400,893, filed Mar. 10, 2009 (Inventor—Arthur D. Craig; Applicant—Dignity Health) (pp. 1-18).
Amendment and Response to Non-Final Office Action filed Feb. 11. 2011 for U.S. Appl. No. 11/693,421, filed Mar. 29, 2007 (Inventor—Arthur D. Craig; Applicant—Dignity Health) (pp. 1-9).
Amendment and Response to Non-Final Office Action filed Feb. 8, 2011 for U.S. Appl. No. 12/400,893, filed Mar. 10, 2009 (Inventor—Arthur D. Craig; Applicant—Dignity Health.) (pp. 1-6).
Amendment and Response to Non-Final Office Action filed Jun. 17, 2010 for U.S. Appl. No. 12/400,893, filed Mar. 10, 2009 (Inventor—Arthur D. Craig; Applicant—Dignity Health) (pp. 1-3).
Amendment and Response to Non-Final Office Action filed Mar. 14, 2012 for U.S. Appl. No. 11/693,499, filed Mar. 29, 2007 (Inventor—Arthur D. Craig; Applicant—Dignity Health) (pp. 1-15).
Amendment and Response to Office Action received Apr. 2, 2012 by the United States Patent and Trademark Office for U.S. Appl. No. 12/400,970, filed Mar. 10, 2009 (Applicant—Dignity Health // Inventor—Arthur Craig) (pp. 1-19).
Amendment and Response to Restriction Requirement filed Jun. 18, 2010 for U.S. Appl. No. 11/693,421, filed Mar. 29, 2007 (Inventor—Arthur D. Craig; Applicant—Dignity Health) (pp. 1-10).
Amendment and Response to Supplemental Final Office Action filed May 27, 2011 for U.S. Appl. No. 11/693,499, filed Mar. 29, 2007 (Inventor—Arthur D. Craig; Applicant—Dignity Health) (pp. 1-18).
Amendment Made Before Examination mailed Dec. 22, 2008 to the European Patent Office for Application 0775971.0 filed Mar. 29, 2007 (Applicant—Catholic Healthcare West // Inventor—Arthur Craig) (pp. 1-10).
Amendment/Req. Reconsideration After Non-Final Rejection issued Aug. 23, 2010 by the United States Patent and Trademark Office for U.S. Appl. No. 11/693,451, filed Mar. 29, 2007 (Applicant—Dignity Health // Inventor—Arthur Craig) (pp. 1-2).
Amendments of Application documents received Jan. 21, 2009 by the European Patent Office for Application 0775972.8 filed Mar. 29, 2007 (Applicant—Dignity Health // Inventor—Arthur Craig) (pp. 1-2).
Amendments Received Before Examination received Dec. 22, 2008 by the European Patent Office for Application 0775972.8 filed Mar. 29, 2007 (Applicant—Dignity Health // Inventor—Arthur Craig) (pp. 1-19).
Applicant Argument/Remarks made in an Amendment received Apr. 22, 2011 by the United States Patent and Trademark Office for U.S. Appl. No. 11/693,451, filed Mar. 29, 2007 (Applicant—Dignity Health // Inventor—Arthur Craig) (pp. 1-12).

(56) References Cited

OTHER PUBLICATIONS

Applicant Argument/Remarks made in an Amendment received Aug. 23, 2010 by the United States Patent and Trademark Office for U.S. Appl. No. 11/693,451, filed Mar. 29, 2007 (Applicant—Dignity Health // Inventor—Arthur Craig) (pp. 1-9).
Disclosure of References issued Sep. 8, 2010 by Canada Patent Office for Application No. 2653110 filed Mar. 29, 2007 (Applicant—Dignity Health // Inventor—Arthur Craig) (pp. 1-29).
Examination Report issued Aug. 7, 2012 for Canadian Patent Application 2,653,110, which was filed Mar. 29, 2007 (Applicant—Dignity Health // Inventor—Arthur Craig) (pp. 1-2).
European Examination Report issued Jun. 6, 2012 for European Patent Application 07759728.4, which was filed Mar. 29, 2007 (Applicant—Dignity Health // Inventor—Arthur Craig) (pp. 1-3).
European Examination Report issued Jun. 16, 2009 for European Patent Application 0759722.7, which was filed Mar. 29, 2007 (Inventor—Arthur D. Craig; Applicant—Dignity Health) (pp. 1-5).
European Examination Report issued Jun. 6, 2012 for European Patent Application 0759722.7, which was filed Mar. 29, 2007 (Inventor—Arthur D. Craig; Applicant—Dignity Health) (pp. 1-3).
Examination Report issued Jan. 28, 2009 by the European Patent Office for Application 0775972.8 (Applicant—Catholic Healthcare West // Inventor—Arthur Craig) (pp. 1-1).
Examination Report issued Jun. 6, 2012 by the European Patent Office for Application 0775971.0 filed Mar. 29, 2007 (Applicant—Catholic Healthcare West // Inventor—Arthur Craig) (pp. 1-3).
Examination Report issued Sep. 8, 2009 by the European Patent Office for Application 0775972.8, which was filed Mar. 29, 2007 (Applicant—Catholic Healthcare West // Inventor—Arthur Craig) (pp. 1-4).
Examination Report issued Nov. 11, 2008 by the European Patent Office for Application 0775971.0 filed Mar. 29, 2007 (Applicant—Catholic Healthcare West // Inventor—Arthur Craig) (pp. 1-2).
Examiner Interview Summary Record issued May 11, 2010 for U.S. Appl. No. 11/693,499, filed Mar. 29, 2007 (Inventor—Arthur D. Craig; Applicant—Dignity Health) (pp. 1-3).
Examiner Interview Summary Record issued May 12, 2010 for U.S. Appl. No. 12/400,893, filed Mar. 10, 2009 (Inventor—Arthur D. Craig; Applicant—Dignity Health) (pp. 1-3).
Examiner's Search Strategy and Results issued Oct. 22, 2010 by the United States Patent and Trademark Office for U.S. Appl. No. 11/693,451, filed Mar. 29, 2007 (Applicant—Dignity Health // Inventor—Arthur Craig) (pp. 1-10).
Examiner's Search Strategy and Results issued Dec. 2, 2011 by the United States Patent and Trademark Office for U.S. Appl. No. 12/400,970, filed Mar. 10, 2009 (Applicant—Dignity Health // Inventor—Arthur Craig) (pp. 1-3).
Final Office Action issued Apr. 8, 2011 for U.S. Appl. No. 11/693,421, filed Mar. 29, 2007 (Inventor—Arthur D. Craig; Applicant—Dignity Health) (pp. 1-8).
Final Office Action issued Jul. 2, 2012 for Japanese Patent Application 2009-503279, which was filed Mar. 29, 2007 (Applicant—// Inventor—) (pp. 1-6).
Final Office Action issued Jul. 16, 2012 for U.S. Appl. No. 12/400,970, filed Mar. 10, 2009 (Applicant—Dignity Health // Inventor—Arthur Craig) (pp. 1-18).
Final Office Action issued Nov. 18, 2011 for U.S. Appl. No. 12/400,893, filed Mar. 10, 2009 (Inventor—Arthur D. Craig; Applicant—Dignity Health) (pp. 1-9).
Final Office Action issued Sep. 28. 2010 for U.S. Appl. No. 11/693,499, filed Mar. 29. (Inventor—Arthur D. Craig; Applicant—Dignity Health)(pp. 1-14).
International Preliminary Report on Patentability issued Sep. 30. 2008 by the International Searching Authority for Application PCT/US2007/065518 filed Mar. 29, 2007 (Applicant—Catholic Healthcare West // Inventor—Arthur Craig) (pp. 1-7).
International Preliminary Report on Patentability issued Sep. 30, 2008 by the International Searching Authority for Application PCT/US2007/065537 filed Mar. 29, 2007 (Applicant—Catholic Healthcare West // Inventor—Arthur Craig) (pp. 1-7).
International Preliminary Report on Patentability issued Sep. 30, 2008 for PCT/US2007/065531, which was filed Mar. 29, 2007 (Inventor—Arthur D. Craig; Applicant—Dignity Health) (pp. 1-7).
International Search Report and Written Opinion issued Sep. 14, 2007 for PCT/US2007/065531, which was filed Mar. 29, 2007 (Inventor—Arthur D. Craig; Applicant—Dignity Health) (pp. 1-10).
International Search Report issued Aug. 30, 2007 by the International Searching Authority for Application PCT/US2007/065518 filed Mar. 29, 2007 (Applicant—Catholic Healthcare West // Inventor—Arthur Craig) (pp. 1-4).
International Search Report issued Aug. 31, 2007 by the International Searching Authority for Application PCT/US2007/065537 filed Mar. 29, 2007(Applicant—Catholic Healthcare West // Inventor—Arthur Craig) (pp. 1-5).
List of References Cited issued Oct. 22, 2010 by the United States Patent and Trademark Office for U.S. Appl. No. 11/693,451, filed Mar. 29, 2007 (Applicant—Dignity Health // Inventor—Arthur Craig) (pp. 1-1).
Non-Final Office Action issued Feb. 15, 2011 for U.S. Appl. No. 12/400,893, filed Mar. 10, 2009 (Inventor—Arthur D. Craig; Applicant—Dignity Health) (pp. 1-9).
Non-Final Office Action issued Jul. 27, 2012 for U.S. Appl. No. 11/693,451, filed Mar. 29, 2007 (Applicant—Dignity Health // Inventor—Arthur Craig) (pp. 1-18).
Non-Final Office Action issued Oct. 14, 2011 for U.S. Appl. No. 11/693,499, filed on Mar. 29, 2007 (Inventor—Arthur D. Craig; Applicant—Dignity Health) (pp. 1-10).
Non-Final Rejection issued Dec. 2, 2011 by the United States Patent and Trademark Office for U.S. Appl. No. 12/400,970, filed Mar. 10, 2009 (Applicant—Dignity Health // Inventor—Arthur Craig) (pp. 1-15).
Notice of Acceptance issued Jan. 13, 2012 for Australian Patent Application No. 2007233135, which was filed on Mar. 29, 2007 (Inventor—Arthur D. Craig; Applicant—Catholic Healthcare West) (pp. 1-3).
Notice of Allowance issued Apr. 3, 2012 for U.S. Appl. No. 11/693,499, filed on Mar. 29, 2007 (Inventor—Arthur D. Craig; Applicant—Dignity Health) (pp. 1-18).
Notice of Allowance issued Dec. 13, 2011 for U.S. Appl. No. 11/693,421, filed Mar. 29, 2007 (Inventor—Arthur D. Craig; Applicant—Dignity Health) (pp. 1-8).
Notice of Allowance issued Jun. 26, 2010 for Japanese Patent Application No. 2009-503285, which was filed Mar. 29, 2006 (Inventor—Arthur D. Craig; Applicant—Dignity Health) (pp. 1-3).
Notice of Allowance issued Jun. 8, 2012 for U.S. Appl. No. 12/400,893, filed Mar. 10, 2009 (Inventor—Arthur D. Craig; Applicant—Dignity Health) (pp. 1-9).
Notice of Allowance issued May 13, 2012 for Israeli Patent Application No. 194406, which was filed Mar. 29, 2007 (Inventor—Arthur D. Craig; Applicant—Dignity Health) (pp. 1-2).
Notice of Reasons for Rejection issued Jan. 5, 2012 by the Japanese Patent Office for Application No. 2009/503279 filed Mar. 29, 2007 (Applicant—// Inventor—) (pp. 1-5).
Notice of References Cited issued Apr. 21, 2010 by the United States Patent and Trademark Office for U.S. Appl. No. 11/693,451, filed Mar. 29, 2007 (Applicant—Dignity Health // Inventor—Arthur Craig) (pp. 1-1).
Office Action issued Jan. 4, 2012 for Japanese Patent Application No. 2009- 503285, which was filed Mar. 29, 2006 (Inventor—Arthur D. Craig; Applicant—Dignity Health) (pp. 1-8).
Official Notice issued Jan. 19, 2012 for Israeli Patent Application No. 194406, which was filed Mar. 29, 2007 (Inventor—Arthur D. Craig; Applicant—Dignity Health) (pp. 1-1).
Response to European Examination Report filed Dec. 8, 2009 for European Patent Application 0759722.7, which was filed Mar. 29, 2007 (Inventor—Arthur D. Craig; Applicant—Dignity Health) (pp. 1-20).
Response to European Examination Report filed Nov. 2, 2010 for European Patent Application 0759722.7, which was filed Mar. 29, 2007 (Inventor—Arthur D. Craig; Applicant—Dignity Health) (pp. 1-16).

(56) References Cited

OTHER PUBLICATIONS

Response to Examiner Report filed Aug. 5, 2012 for Israeli Patent Application 194407 (Applicant—Dignity Health // Inventor—Arthur Craig) (pp. 1-12).
Response to Examination Report mailed Jan. 14, 2010 to the European Patent Office for Application 0775972.8 (Applicant—Catholic Healthcare West // Inventor—Arthur Craig) (pp. 1-28).
Response to Examination Report mailed Oct. 15, 2010 to the European Patent Office for Application 0775971.0 filed Mar. 29, 2007 (Applicant—Catholic Healthcare West // Inventor—Arthur Craig) (pp. 1-16).
Response to Examination Report mailed Oct. 20, 2009 to the European Patent Office for Application 0775971.0 filed Mar. 29, 2007 (Applicant—Catholic Healthcare West // Inventor—Arthur Craig) (pp. 1-21).
Response to Examination received Dec. 22, 2011 by IP Australia for Application No. 2007233205 filed Mar. 29, 2007 (Applicant—Catholic Healthcare West // Inventor—Arthur Craig) (pp. 1-23).
Response to Final Office Action filed Sep. 1, 2011 for U.S. Appl. No. 11/693,499, filed Mar. 29, 2007 (Inventor—Arthur D. Craig; Applicant—Dignity Health) (pp. 1-18).
Response to First Examination Report filed Dec. 22, 2011 for Australian Patent Application No. 2007233135, which was filed on Mar. 29, 2007 (Inventor—Arthur D. Craig; Applicant—Dignity Health) (pp. 1-23).
Response to Office Action filed Jun. 4, 2012 for Japanese Patent Application No. 2009-503285, which was filed Mar. 29, 2006 (Inventor—Arthur D. Craig; Applicant—Dignity Health) (pp. 1-4).
Response to Official Notice filed Jan. 29, 2012 for Israeli Patent Application No. 194406, which was filed Mar. 29, 2007 (Inventor—Arthur D. Craig; Applicant—Dignity Health) (pp. 1-1).
Supplemental Final Office Action issued Mar. 1, 2011 for U.S. Appl. No. 11/693,499, filed Mar. 29, 2007 (Inventor—Arthur D. Craig; Applicant—Dignity Health) (pp. 1-14).
Written Opinion issued Aug. 30, 2007 by the International Searching Authority for Application PCT/US2007/065518 filed Mar. 29, 2007 (Applicant—Catholic Healthcare West // Inventor—Arthur Craig) (pp. 1-6).
Written Opinion issued Aug. 31, 2007 by the International Searching Authority for Application PCT/US2007/065537 filed Mar. 29, 2007 (Applicant—Catholic Healthcare West // Inventor—Arthur Craig)(pp. 1-6).
Israeli Patent Application No. 194406: Official Action issued by the State of Israel Department of Justice on Oct. 20, 2010, 4 pages.
Israeli Patent Application No. 194407: Official Action issued by the State of Israel Department of Justice on Oct. 21, 2010, 4 pages.
Final Office Action in U.S. Appl. No. 11/693,451, Mailing Date: Oct. 22, 2010.
Issue Notification issued Mar. 14, 2012 for U.S. Appl. No. 11/693,421, filed Mar. 29, 2007 (Inventor—Arthur D. Craig; Applicant—Dignity Health) (pp. 1-1).
Issue Notification issued Sep. 12, 2012 for U.S. Appl. No. 12/400,893, filed Mar. 10, 2009 (Inventor—Arthur D. Craig; Applicant—Dignity Health) (pp. 1-1).
Request for Continued Examination filed Feb. 8, 2011 for U.S. Appl. No. 12/400,893, filed Mar. 10, 2009 (Inventor—Arthur D. Craig; Applicant—Dignity Health) (pp. 1-3).
Supplemental Non-Final Office Action issued Feb. 23, 2011 for U.S. Appl. No. 12/400,893, filed Mar. 10, 2009 (Inventor—Arthur D. Craig; Applicant—Dignity Health) (pp. 1-9).
Non-Final Office Action issued Jun. 19, 2013 for U.S. Appl. No. 13/438,645, filed Apr. 3, 2012 (Inventor—Arthur D. Craig; Applicant—Dignity Health) (pp. 1-18).
Response to Restriction/Election Requirement filed Apr. 10, 2013 for U.S. Appl. No. 13/438,645, filed Apr. 3, 2012 (Inventor—Arthur D. Craig; Applicant—Dignity Health) (pp. 1-11).
Restriction/Election Requirement issued Feb. 11, 2013 for U.S. Appl. No. 13/438,645, filed Apr. 3, 2012 (Inventor—Arthur D. Craig; Applicant—Dignity Health) (pp. 1-5).
Issue Notification issued Jun. 20, 2012 for U.S. Appl. No. 11/693,499, filed Mar. 29, 2007 (Inventor—Arthur D. Craig; Applicant—Dignity Health) (pp. 1-1).
Amendment and Response to Final Office Action filed May 9, 2011 for U.S. Appl. No. 12/401,026, filed Mar. 10, 2009 (Inventor—Arthur D. Craig; Applicant—Dignity Health) (pp. 1-22).
Amendment and Response to Non-Final Office Action filed Aug. 19, 2010 for U.S. Appl. No. 12/401,026, filed Mar. 10, 2009 (Inventor—Arthur D. Craig; Applicant—Dignity Health) (pp. 1-24).
Final Office Action issued on Nov. 15, 2010 for U.S. Appl. No. 12/401,026, filed Mar. 10, 2009 (Inventor—Arthur D. Craig; Applicant—Dignity Health) (pp. 1-17).
Non-Final Office Action issued Apr. 19, 2010 for U.S. Appl. No. 12/401,026, filed Mar. 10, 2009 (Inventor—Arthur D. Craig; Applicant—Dignity Health) (pp. 1-18).
Non-Final Office Action issued Jun. 19, 2013 for U.S. Appl. No. 12/401,026, filed Mar. 10, 2009 (Inventor—Arthur D. Craig; Applicant—Dignity Health) (pp. 1-13).
Amendment and Response to Non-Final Office Action filed on Jan. 25, 2013 for U.S. Appl. No. 11/693,451, filed Mar. 29, 2007 (Inventor—Arthur D. Craig; Applicant—Dignity Health) (pp. 1-13).
Amendment in Response to Final Office Action filed Jul. 26, 2013 for U.S. Appl. No. 11/693,451, filed Mar. 29, 2007 (Inventor—Arthur D. Craig; Applicant—Dignity Health) (pp. 1-7).
Applicant-Initiated Interview Summary issued Feb. 22, 2013 for U.S. Appl. No. 11/693,451, filed Mar. 29, 2007 (Inventor—Arthur D. Craig; Applicant—Dignity Health) (pp. 1-3).
Final Office Action issued May 16, 2013 for U.S. Appl. No. 11/693,451, filed Mar. 29, 2007 (Inventor—Arthur D. Craig; Applicant—Dignity Health) (pp. 1-11).
Final Office Action issued on Oct. 22, 2010 for U.S. Appl. No. 11/693,451, filed Mar. 29, 2007 (Inventor—Arthur D. Craig; Applicant—Dignity Health) (pp. 1-15).
Notice of Allowance issued Aug. 19, 2013 for U.S. Appl. No. 11/693,451, filed Mar. 29, 2007 (Inventor—Arthur D. Craig; Applicant—Dignity Health) (pp. 1-6).
Supplemental Amendment in Response to Non-Final Office Action filed Mar. 21, 2013 for U.S. Appl. No. 11/693,451, filed Mar. 29, 2007 (Inventor—Arthur D. Craig; Applicant—Dignity Health) (pp. 1-9).
Supplemental Amendment to Final Office Action filed Aug. 9, 2013 for U.S. Appl. No. 11/693,451, filed Mar. 29, 2007 (Inventor—Arthur D. Craig; Applicant—Dignity Health) (pp. 1-10).
Amendment and Response filed Jan. 16, 2013 for U.S. Appl. No. 12/400,970, filed Mar. 10, 2009 (Inventor—Arthur D. Craig; Applicant—Dignity Health) (pp. 1-13).
Amendment in Response to Office Action filed Jun. 14, 2013 for U.S. Appl. No. 12/400,970, filed Mar. 10, 2009 (Inventor—Arthur D. Craig; Applicant—Dignity Health) (pp. 1-8).
Applicant Initiated Interview Summary issued Feb. 25, 2013 for U.S. Appl. No. 12/400,970, filed Mar. 10, 2009 (Inventor—Arthur D. Craig; Applicant—Dignity Health) (pp. 1-3).
Non-Final Office Action issued Mar. 28, 2013 for U.S. Appl. No. 12/400,970, filed Mar. 10, 2009 (Inventor—Arthur D. Craig; Applicant—Dignity Health) (pp. 1-12).
Request for Continued Examination filed Jan. 16, 2013 for U.S. Appl. No. 12/400,970, filed Mar. 10, 2009 (Inventor—Arthur D. Craig; Applicant—Dignity Health) (pp. 1-3).
Supplemental Amendment in Response to Final Office Action filed Mar. 21, 2013 for U.S. Appl. No. 12/400,970, filed Mar. 10, 2009 (Inventor—Arthur D. Craig; Applicant—Dignity Health) (pp. 1-10).
Response to Final Office Action filed Feb. 6, 2014 for U.S. Appl. No. 13/438,645, which was filed on Apr. 3, 2012 (Inventor—Arthur D. Craig; Applicant—Dignity Health) (pp. 1-14).
Request for Continued Examination filed Feb. 6, 2014 for U.S. Appl. No. 13/438,645, which was filed on Apr. 3, 2012 (Inventor—Arthur D. Craig; Applicant—Dignity Health) (pp. 1-3).
Non-Final Office Action issued Mar. 21, 2014 for U.S. Appl. No. 13/438,645, which was filed on Apr. 3, 2012 (Inventor—Arthur D. Craig; Applicant—Dignity Health) (pp. 1-12).
Issue Notification issued Feb. 5, 2014 for U.S. Appl. No. 12/400,970, which was filed Mar. 10, 2009 (Inventor—Arthur D. Craig; Applicant—Dignity Health) (pp. 1-1).

(56) References Cited

OTHER PUBLICATIONS

Preliminary Amendment filed Feb. 18, 2014 for U.S. Appl. No. 14/089,185, which was filed Nov. 25, 2013 (Inventor—Arthur D. Craig; Applicant—Dignity Health) (pp. 1-44).

Preliminary Amendment filed Jan. 10, 2014 for U.S. Appl. No. 14/152,428, which was filed Jan. 10, 2014 (Inventor—Arthur D. Craig; Applicant—Dignity Health) (pp. 1-5).

* cited by examiner

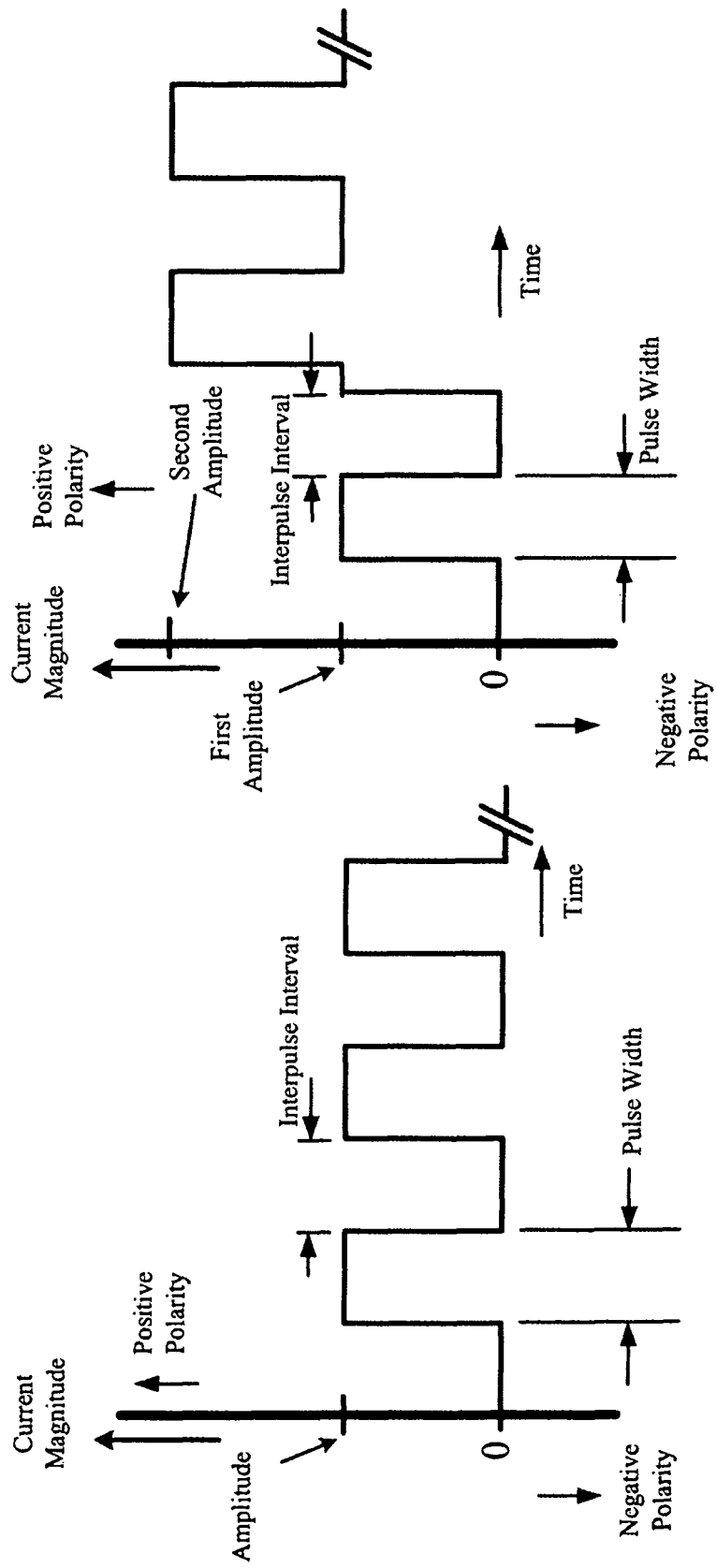

SYNCHRONIZATION OF VAGUS NERVE STIMULATION WITH THE CARDIAC CYCLE OF A PATIENT

CROSS-REFERENCE TO RELATED APPLICATIONS

This application is a continuation of U.S. application Ser. No. 11/693,499, filed Mar. 29, 2007, now issued as U.S. Pat. No. 8,219,188,and which itself claims the benefit of U.S. Provisional Application No. 60/787,680, filed Mar. 29, 2006, now expired.

U.S. patent application Ser. No. 11/693,451 entitled "Microburst Electrical Stimulation Of Cranial Nerves For The Treatment Of Medical Conditions", by Arthur D. Craig and filled on Mar. 29, 2007 is hereby incorporated herein by reference.

PCT patent application Ser. No. PCT/US 07/65537 entitled "Vagus Nerve Stimulayion Mthod" by Arthur D.Craig and filled on Mar. 29,2007 is hereby incorporated herein by reference.

BACKGROUND OF THE INVENTION

1. Field of the Invention

This invention relates generally to medical device systems and, more particularly, to medical device systems for applying electrical signals to a cranial nerve for the treatment of medical conditions, and for improved electrical signals in such systems.

2. Description of the Related Art

Many advancements have been made in treating diseases such as depression and epilepsy. Therapies using electrical signals for treating these diseases have been found to effective. Implantable medical devices have been effectively used to deliver therapeutic stimulation to various portions of the human body (e.g., the vagus nerve) for treating these diseases. As used herein, "stimulation" or "stimulation signal" refers to the application of an electrical, mechanical, magnetic, electro-magnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a medical condition by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuro-plasticity or neurogenesis of brain tissue.

In some embodiments, electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. The electrical signal may be applied by an IMD that is implanted within the patient's body. In other cases, the signal may be generated by an external pulse generator outside the patient's body, coupled by an RF or wireless link to an implanted electrode.

Generally, neurostimulation signals that perform neuromodulation are delivered by the IMD via one or more leads. The leads generally terminate at their distal ends in one or more electrodes, and the electrodes, in turn, are electrically coupled to tissue in the patient's body. For example, a number of electrodes may be attached to various points of a nerve or other tissue inside a human body for delivery of a neurostimulation signal.

While feedback stimulation schemes have been proposed, conventional vagus nerve stimulation (VNS) usually involves non-feedback stimulation characterized by a number of parameters. Specifically, convention vagus nerve stimulation usually involves a series of electrical pulses in bursts defined by an "on-time" and an "off-time." During the on-time, electrical pulses of a defined electrical current (e.g., 0.5-2.0 milliamps) and pulse width (e.g., 0.25-1.0 milliseconds) are delivered at a defined frequency (e.g., 20-30 Hz) for the on-time duration, usually a specific number of seconds, e.g., 10-100 seconds. The pulse bursts are separated from one another by the off-time, (e.g., 30 seconds-5 minutes) in which no electrical signal is applied to the nerve. The on-time and off-time parameters together define a duty cycle, which is the ratio of the on-time to the combination of the on-time and off-time, and which describes the percentage of time that the electrical signal is applied to the nerve.

In conventional VNS, the on-time and off-time may be programmed to define an intermittent pattern in which a repeating series of electrical pulse bursts are generated and applied to the vagus nerve. Each sequence of pulses during an on-time may be referred to as a "pulse burst." The burst is followed by the off-time period in which no signals are applied to the nerve. The off-time is provided to allow the nerve to recover from the stimulation of the pulse burst, and to conserve power. If the off-time is set at zero, the electrical signal in conventional VNS may provide continuous stimulation to the vagus nerve. Alternatively, the idle time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in conventional VNS may be programmed over a range of values. The pulse width for the pulses in a pulse burst of conventional VNS may be set to a value not greater than about 1 msec, such as about 250-500 µsec, and the number of pulses in a pulse burst is typically set by programming a frequency in a range of about 20-150 Hz (i.e., 20 pulses per second to 150 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Various feedback stimulation schemes have been proposed. In U.S. Pat. No. 5,928,272, the automatic activation of a neurostimulator such as a vagus nerve stimulator is described based on a detected increase in heart rate. The '272 patent notes that epilepsy attacks are sometimes preceded by increases in heart rate and proposes automatically applying an electrical signal to a vagus nerve if the patient's heart rate exceeds a certain level. The patent does not disclose initiating or synchronizing the therapeutic electrical signal with the patient's heart rhythms. Instead, detection of an abnormal heart rate is used to trigger otherwise conventional VNS.

A new type of stimulation has been proposed known as "microburst"stimulation, which provides enhanced evoked potentials in the brain (as more fully described in co-pending application Ser. No. 11/693,451, "Microburst Electrical Stimulation Of Cranial Nerves For The Treatment Of Medical Conditions"). "Enhanced" in this context refers to electrical potentials evoked in the forebrain by neurostimulation that are higher than those produced by conventional neurostimulation. The electrical signal for this improved therapy is substantially different from the electrical signals in conventional VNS. In particular, electrical signals in microburst stimulation are characterized by very short bursts of a limited number of electrical pulses. These shorts bursts of less than 1 second are referred to hereinafter as "microbursts." By applying an electrical signal comprising a series of microbursts to, for example, a vagus nerve of a patient, enhanced vagal evoked potentials (eVEP) are produced in therapeutically significant areas of the brain. Significantly, eVEP are not produced by conventional vagus nerve stimulation.

As used herein, the term "microburst" refers to a portion of a therapeutic electrical signal comprising a limited plurality of pulses and a limited burst duration. More particularly, a microburst may comprise at least two but no more than 25 electrical pulses, and may last for no more than 1 second, and typically less than 100 milliseconds, more typically 10-80 msec. A therapeutic electrical signal may comprise a series of microbursts separated from one another by time intervals known as "interburst periods" which allow a refractory interval for the nervous system to recover from the microburst and again become receptive to eVEP stimulation by another microburst. In some embodiments, the interburst period may be as long as or longer than the adjacent microbursts separated by the interburst period. In some embodiments the interburst period may comprise an absolute time period of at least 100 milliseconds and in some embodiments, up to 6 seconds. Adjacent pulses in a microburst are separated by a time interval known as an "interpulse interval," which may comprise a time period from 1 msec to 50 msec. The interpulse interval, together with the number of pulses and the pulse width of each pulse, determines a "microburst duration," which is the length of a microburst from the beginning of the first pulse to the end of the last pulse (and thus the beginning of a new interburst period). Microburst duration in microburst stimulation can be 1 second or less (i.e., microbursts can be no greater than 1 second), and more preferably is 100 msec or less, and still more preferably is in the range of 10-80 msec. The pulses in a microburst may be further characterized by a current amplitude and a pulse width. Microburst stimulation may optionally include an on-time and an off-time in which the microbursts are provided and not provided, respectively, to a cranial nerve. At least one of the interburst period, the number of pulses per burst, the interpulse interval, the microburst duration, the current amplitude, the pulse width, the on-time, or the off-time are selected to enhance cranial nerve evoked potentials.

The timing of neurostimulation signals has heretofore generally conformed to standard clock cycles, without regard to the efficacy of neurostimulation signals delivered at particular time-points. The present inventor is unaware of previous investigations of the efficacy of neurostimulation signals delivered at particular time-points of physiological cycles.

SUMMARY OF THE INVENTION

In one embodiment, the present invention provides a method of treating a medical condition of a patient using an implantable medical device, comprising detecting said patient's cardiac cycle and applying an electrical signal to a portion of a vagus nerve of said patient through an electrode at a selected point in the cardiac cycle, to treat the medical condition.

In one embodiment, the present invention is a method of treating a medical condition of a patient, comprising: coupling at least one electrode to at least one vagus nerve of the patient, providing a programmable electrical signal generator coupled to the electrode, detecting said patient's cardiac cycle, generating an electrical signal with the electrical signal generator, and applying the electrical signal to the electrode to treat the medical condition, and wherein the applying the electrical signal at a selected point in the cardiac cycle.

Applying an electrical signal at a selected point in a physiological cycle may be referred to herein as "synchronizing" the electrical signal with the physiological cycle. Synchronizing does not require modification of one or more electrical signal parameters to match one or more parameters of the physiological cycle.

In one embodiment, the present invention is a computer readable program storage device encoded with instructions that, when executed by a computer, perform a method comprising: detecting said patient's cardiac cycle, generating an electrical signal with the electrical signal generator, and applying the electrical signal to an electrode coupled to at least one vagus nerve of the patient to treat the medical condition, and wherein applying the electrical signal to the vagus nerve occurs at a selected point in the cardiac cycle.

In one aspect, the present invention relates to a medical condition treatment system comprising at least one electrode coupled to at least one vagus nerve of a patient, an implantable device operatively coupled to the electrode and comprising an electrical signal generator capable of applying an electrical signal to the vagus nerve at a selected point in the patient's cardiac cycle, and a device operatively coupled to the electrode and capable of detecting said patient's cardiac cycle.

In another alternate embodiment, the method may comprise alternating first and second time periods, wherein in the first time period a conventional vagus nerve stimulation electrical signal is applied to a vagus nerve of a patient, and a second time period in which microburst electrical signals are applied to a vagus nerve of a patient. The conventional vagus nerve stimulation signal may be defined by a current amplitude, a pulse width, a frequency, an on-time and an off-time. In one embodiment, the first time period (in which the conventional VNS electrical signal is applied to the vagus nerve) corresponds to the on-time and the second time period (in which the microburst electrical signal is applied to the vagus nerve), corresponds to the off-time of the conventional vagus nerve signal.

In any embodiment, the selected point in the cardiac cycle can be a point in the cardiac cycle correlated with increased afferent conduction on the vagus nerve, such as a point from about 10 msec to about 800 msec after an R-wave of the patient's ECG. In a particular embodiment, the selected point in the cardiac cycle occurs from about 10-800 msec after an R-wave during inspiration by the patient. In a different embodiment, the selected point in the cardiac cycle occurs from about 10-800 msec after an R-wave during expiration by the patient. In a further embodiment, the selected point in the cardiac cycle occurs from about 10-500 msec after an R-wave of the patient's ECG, which may further occur during inspiration, expiration, or without regard to respiration. In another embodiment, the selected point in the cardiac cycle can be a point in the cardiac cycle when said applying increases heart rate variability.

In one embodiment, the present invention is a method of treating a medical condition of a patient, comprising: coupling at least one electrode to at least one vagus nerve of the patient, providing a programmable electrical signal generator coupled to the electrode, detecting said patient's respiratory cycle, generating an electrical signal with the electrical signal generator, and applying the electrical signal to the electrode to treat the medical condition, and wherein the applying the electrical signal at a selected point in the respiratory cycle.

In a further embodiment, the present invention is a method of treating a medical condition of a patient, comprising: coupling at least one electrode to at least one vagus nerve of the patient, providing a programmable electrical signal generator coupled to the electrode, detecting said patient's respiratory cycle and cardiac cycle, generating an electrical signal with the electrical signal generator, and applying the electrical signal to the electrode to treat the medical condition, and wherein the applying the electrical signal at a selected point in the respiratory cycle and/or cardiac cycle.

BRIEF DESCRIPTION OF THE DRAWINGS

The invention may be understood by reference to the following description taken in conjunction with the accompanying drawings, in which like reference numerals identify like elements, and in which:

FIGS. 4A, 4B, and 4C illustrate exemplary waveforms for generating the electrical signals for stimulating the vagus nerve for treating a medical condition, according to one illustrative embodiment of the present invention;

Figure 1:
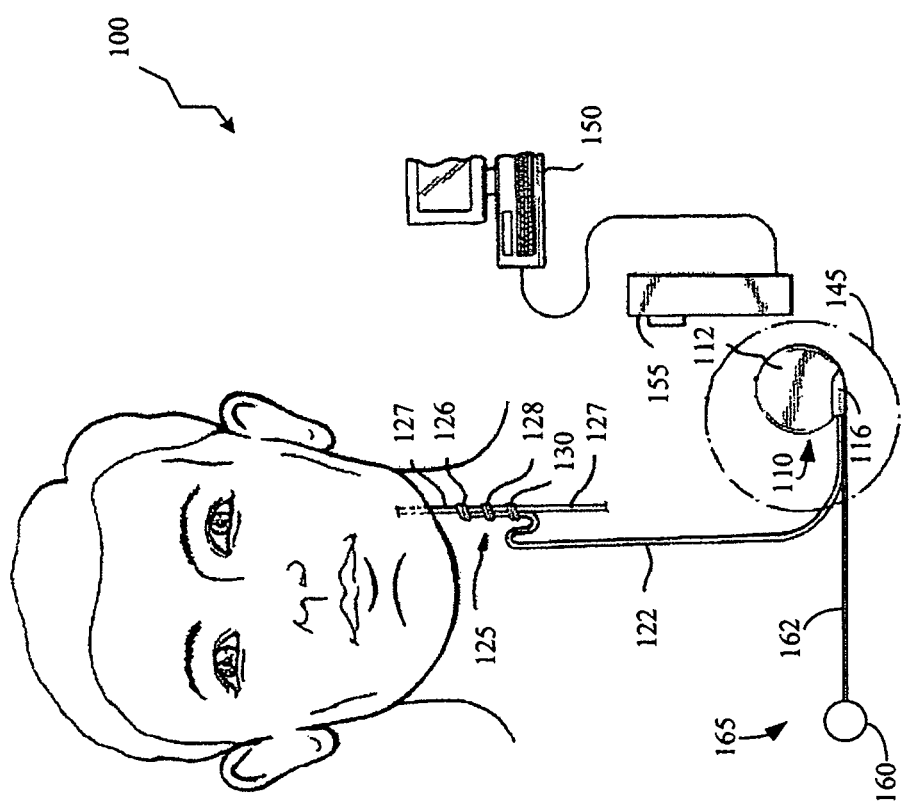
FIG. 1 provides a stylized diagram of an implantable medical device implanted into a patient's body for providing a therapeutic electrical signal to a neural structure of the patient's body, in accordance with one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium there between. The presence of small quantities of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation has been proposed to treat a number of medical conditions pertaining to or mediated by one or more structures of the nervous system of the body, including epilepsy and other movement disorders, depression, anxiety disorders and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pats. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous medical conditions for which cranial nerve stimulation has been proposed or suggested as a treatment option, the fact that detailed neural pathways for many (if not all) cranial nerves remain relatively unknown, makes predictions of efficacy for any given medical condition difficult or impossible. Moreover, even if such pathways were known, the precise stimulation parameters that would modulate particular pathways relevant to a particular medical condition generally cannot be predicted.

In one embodiment, the present invention relates to a method of treating a medical condition selected from the group consisting of epilepsy, neuropsychiatric disorders (including but not limited to depression), eating disorders/obesity, traumatic brain injury/coma, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, and reproductive endocrine disorders (including fertility) in a patient.

The present invention relates to synchronization of cranial nerve electrical stimulation to a physiological event, such as a specific point in the cardiac cycle and/or respiratory cycle. Synchronization of such electrical stimulation signals may, in one embodiment, be performed by an implantable medical device (IMD) system. An IMD system may comprise an implantable medical device for delivering a therapeutic electrical signal and sensing/recording data, and an external device (ED) capable of programming and/or data transfer operations with the IMD.

The medical device system of the present invention provides for software module(s) that are capable of acquiring, storing, and processing one or more forms of data, such as patient data/parameters (e.g., physiological data such as heart rate, cardiac cycle data and respiration cycle data, side-effects data, brain-activity data, disease progression or regression data, self-evaluation data, seizure characteristic data, quality of life data, etc.) and therapy parameter data. Therapy parameters may include, but are not limited to, electrical signal parameters that define the therapeutic electrical signals delivered by the medical device, medication parameters (e.g., dosages, frequency of medication provided to the patient, etc.) and/or any other therapeutic treatment parameter. In an alternative embodiment, the term "therapy parameters" may refer to electrical signal parameters defining the therapeutic electrical signals delivered by the medical device. Therapy parameters for a therapeutic electrical signal may also include, but are not limited to, an interburst period, a number of pulses per burst, an interpulse interval, a burst duration, a current amplitude, a pulse width, a pulse frequency, a signal on-time, a signal off-time, and/or a duty cycle.

Although not so limited, a system capable of implementing embodiments of the present invention is described below. FIG. 1 depicts a stylized implantable medical device (IMD) 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145), similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes. In one embodiment, the electrode assembly 125 comprises at least a cathode and an anode. In another embodiment, the electrode assembly comprises one or more unipolar electrodes.

Lead assembly 122 is attached at its proximal end to connectors on the header 116 of generator 110. The electrode assembly 125 may be surgically coupled to a vagus nerve 127 in the patient's neck or at another location, e.g., near the patient's diaphragm or at the esophagus/stomach junction. Other (or additional) cranial nerves such as the trigeminal and/or glossopharyngeal nerves may also be used to deliver the electrical signal in particular alternative embodiments. In one embodiment, the electrode assembly 125 comprises a bipolar stimulating electrode pair 126, 128 (i.e., a cathode and an anode). Suitable electrode assemblies are available from Cyberonics, Inc., Houston, Tex., USA as the Model 302 electrode assembly. However, persons of skill in the art will appreciate that many electrode designs could be used in the present invention. In one embodiment the two electrodes are wrapped about the vagus nerve 127, and the electrode assembly 125 may be secured to the vagus nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 may be secured, while retaining the ability to flex with movement of the chest and neck, by a suture connection to nearby tissue (not shown).

In some embodiments, the electrode assembly 125 may comprise temperature sensing elements, heart rate or cardiac cycle sensor elements, and/or respiration cycle sensing elements. In one embodiment, the electrode assembly 125 comprises a strain gauge that may be used to determine inspiration by identifying chest expansion. By detecting the onset of chest expansion, the strain gauge may detect the onset of inspiration. The strain gauge may also detect expiration by identifying when the chest is contracting. Other sensors for other body parameters may also be employed to trigger active stimulation. Both passive and active stimulation may be combined or delivered by a single IMD according to the present invention. Either or both modes may be appropriate to treat a specific patient under observation.

In one embodiment, a sensor assembly 165, comprising a sensor lead assembly 162 and a sensor 160, may be employed to detect a body parameter of the patient, such as a parameter related to the patient's cardiac cycle. The sensor 160 may be one or more electrocardiogram leads or a heart rate monitor, among other sensing devices.

The electrical pulse generator 110 may be programmed with an external device (ED) such as computer 150 using programming software known in the art. A programming wand 155 may be coupled to the computer 150 as part of the ED to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

The IMD 100 may detect one or more portions of patient's cardiac cycle, e.g., P waves, R waves, R-R interval, QRS complex, T waves, etc., or the entire PQRST cycle. In response to detecting the one or more portions of the cardiac cycle, the IMD 100 may cause the pulse generator 110 to deliver an electrical signal via leads 122 to a cranial nerve such as vagus nerve 127 at a particular point during the cardiac cycle. For example, a sensor 160, such as a heart rate monitor or a set of electrocardiogram (ECG) leads, may be used to detect the one or more portions of the patient's cardiac cycle. The detected portion of the cardiac cycle may then be used to trigger the pulse generator 110 to generate the therapeutic electrical signal and apply the signal to the vagus nerve 127.

A "cardiac cycle" herein refers to the electrical activity of a patient's heart that occurs in the period between the onset of consecutive P waves. This electrical activity may be measured and analyzed by an electrocardiogram (ECG). The cycle begins with the P wave, which corresponds to electrical depolarization of the atria of the heart. As is known, an electrocardiogram exhibits a P wave, a QRS complex, and a T wave, and in some patients it may also exhibit a U wave. An isoelectric baseline follows from the end of the T or U wave to the onset of the next P wave with the patient's next heartbeat.

Figure 8:
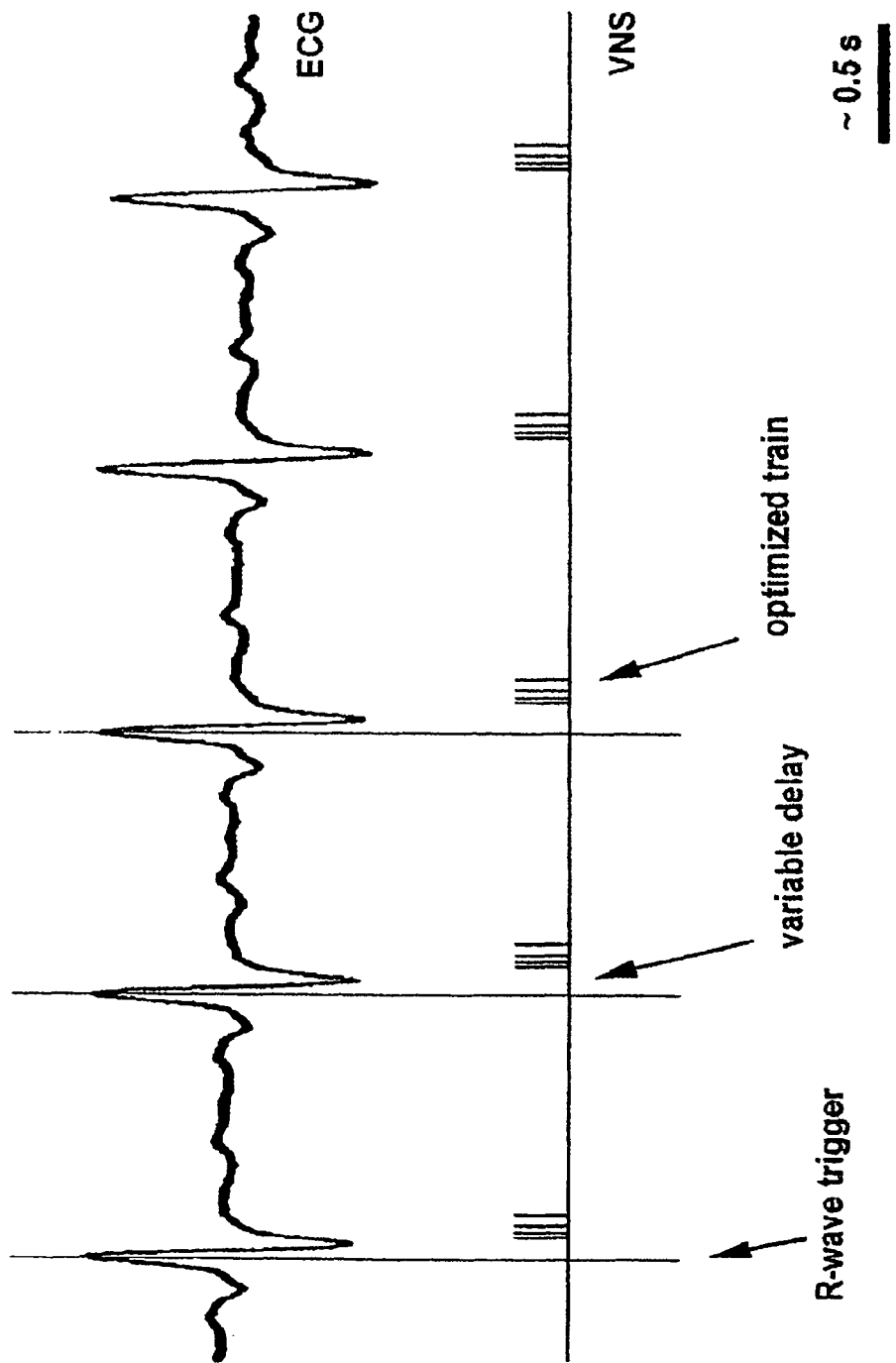
FIG. 8 illustrates synchronization of a vagal stimulus burst to the QRS wave of a patient's ECG.

According to one aspect of the present invention, conventional bursts and/or microbursts of electrical pulses comprising an electrical signal are applied to the vagus nerve in synchronization with one or more portions of the cardiac cycle. In one embodiment, the electrical signal is synchronized with the R wave of a patient's cardiac cycle. In another embodiment, the signal is synchronized with the QRS complex. In a further embodiment, the signal is further synchronized with the respiration cycle of the patient. In a still further embodiment, the therapeutic electrical signal is synchronized with both a portion of the patient's cardiac cycle and the respiration cycle of the patient. Synchronization of the application of the therapeutic electrical signal with the patient's cardiac and/or respiration cycles enables the IMD to augment endogenous cardiac-related and/or respiration-related vagal afferent activity with the exogenous electrical signal. In one embodiment, as illustrated in FIG. 8, the neurostimulation burst is triggered by the R-wave of the ECG after a delay period, which comprises a predetermined or random time interval that may range, e.g., from ~10-800 msec following detection of the R-wave. In another embodiment, the therapeutic electrical signal is applied to the vagus nerve after a predetermined or random time interval, e.g. ~10-1000 msec following the beginning of inspiration by the patient. In one further embodiment, the IMD 100 applies an electrical signal to a cranial nerve, such as vagus nerve 127, beginning at a point from about 10 msec to about 800 msec after an R-wave of the patient's ECG when the patient is inspiring. Without being bound by theory, it is believed that synchronizing the application of the exogenous therapeutic electrical signal to the vagus nerve with the detection of the R-wave of the patient's cardiac cycle and/or the beginning of inspiration by the patient may increase the efficacy of neurostimulation therapy by entraining the exogenous signal with the endogenous cyclic facilitation of central vagal afferent pathways.

In one embodiment, a first electrical signal is applied in synchrony with the patient's cardiac and/or respiratory cycles, as described above, and a second electrical signal is applied without reference to the patient's physiological cycle, wherein the second electrical signal differs from the first in at least one parameter selected from the group consisting of a burst duration, a number of pulses per burst, an interpulse interval, an interburst period, a current magnitude, a pulse frequency, a signal width, an on-time, and an off-time.

In another embodiment, the synchronization of the exogenous electrical signal further comprises not providing the exogenous signal during periods in the opposite half of the cardiac and/or respiratory duty cycles, when the central pathways are inhibited. Again without being bound by theory, it is believed that asynchronously-applied neurostimulation signals in other portions of the cardiac and/or respiratory cycles may be less effective because endogenous signals in those portions of the cardiac and/or respiratory cycles are less significant, in terms of their information content, for modulating those portions of the brain relevant to homeostasis mechanisms implicated in medical conditions such as epilepsy and depression, among others. Thus, at least a portion of the exogenous electrical signal in conventional stimulation algorithms may be therapeutically irrelevant, or even counterproductive.

Accordingly, in one embodiment, the therapeutic electrical signal burst or microburst is applied to the cranial nerve, such as the vagus nerve 127, after a delay period of, e.g., ~10-800 msec following detection of the R-wave, and no signal is applied during the remaining portions of one or more subsequent cardiac cycles. In another embodiment, the therapeutic electrical signal is applied to the vagus nerve after a delay period of ~10-1000 msec following the beginning of inspiration by the patient, and no signal is applied to the nerve during the remaining portions of the respiration cycle. In still another embodiment, the therapeutic electrical signal is applied to the vagus nerve after a delay period following detection of the R-wave only if the patient is inspiring, and otherwise no signal is applied to the vagus nerve.

A patient's heart rate can vary due to a number of reasons, including variations in activity level (e.g., exercise or other exertion), variations in emotional state, or variations in breathing, among others. In generally healthy patients, heart rate variability (HRV) of about 0.15 Hz to about 0.4 Hz is observed with respiration (breathing), with heart rate increasing during inspiration (inhalation) and decreasing during expiration (exhaling). HRV can decrease or increase greatly during meditation, and can increase by the practice of slow, paced breathing. Observers have noted a correlation between respiration-related HRV of about 0.15 Hz to about 0.4 Hz and physical health, including greater immune function, lower incidence of cardiac arrhythmia, and a greater prevalence of commonly-preferred emotional states (e.g., more "happiness" and less "sadness") relative to persons having respiration-related HRV below 0.15 Hz. Consequently, it may be beneficial for the patient to begin paced breathing during the pulse burst. Further, it may improve the efficacy of the exogenous electrical signal if the pulses are triggered while the patient is performing paced breathing. The beneficial effects of the paced breathing coupled with the therapeutic effects of the microbursts may increase the efficacy of the stimulation. Respiration-related HRV can be determined by monitoring heart rate or electrocardiography and calculating intervals between heart beats or particular points in consecutive cardiac cycles, such as consecutive R-waves. The variations in HRV can be used to indicate periods when the R-R interval is decreasing (corresponding to inspiration as the heart rate accelerates, thus reducing the duration of R-R interval relative to the prior R-R interval) or increasing (corresponding to expiration as the heart rate decelerates, thus increasing the R-R interval duration relative to the prior R-R interval). Alternatively, the IMD system 100 may detect the high frequency (0.18-0.4 Hz) component of the HRV power spectrum to determine when inspiration occurs. It will be appreciated that different techniques to detect cardiac cycles and respiration may be used, including separate sensors for heart rate and breathing, and that all such techniques are within the scope of the present invention.

In one embodiment, the IMD 100 applies a therapeutic electrical signal to the cranial nerve, such as the vagus nerve 127, at a point in the cardiac cycle correlated with increased afferent conduction on the cranial nerve, such as the vagus nerve 127. This may be done by sensing electrical activity on the vagus nerve and initiating the therapeutic electrical signal when the electrical activity increases. Without being bound by theory, since it is believed that increased electrical activity corresponds with inspiration and/or appropriate portions of the cardiac cycle, such a technique could result in supplementing the endogenous central vagal activity relevant to the patient's medical condition with the therapeutic, exogenous electrical signal.

In one embodiment, the IMD 100 applies an electrical signal to the cranial nerve, such as the vagus nerve 127, at a point in the cardiac cycle when applying the signal increases heart rate variability. In one further embodiment, the IMD 100 applies an electrical signal to the cranial nerve, such as the vagus nerve 127, beginning at a point from about 10 msec to about 800 msec after an R-wave of the patient's ECG during expiration (exhalation) by the patient.

In one embodiment, the IMD 100 does not apply an electrical signal to the cranial nerve, such as the vagus nerve 127, at a point during the cardiac cycle correlated with increased efferent conduction on the cranial nerve.

In one embodiment, stimulation may be applied to generate efferent electrical activity on the nerve, which refers to signals traveling on a nerve in a direction away from the central nervous system. In another embodiment, a "blocking" type of electrical signal may be employed using the IMD 100, such that both afferent and efferent electrical activity on the nerve is prevented from traveling further. Thus, the IMD 100 may operate to "silence" the vagus nerve.

Further, or alternatively, afferent stimulation may also be performed, wherein afferent fibers are stimulated while efferent fibers are not stimulated or are blocked. Afferent stimulation may be especially potent at times when the nerve conducts a relatively large number of afferent signals. For the vagus nerve, an example of such a time is about 10 msec to about 800 msec after the R-wave of the cardiac cycle.

In addition to electrical signals to generate efferent or afferent electrical activity on the nerve, the blocking type of stimulation described above may also be applied to the nerve. Efferent blocking may be realized by enhancing the hyper polarization of a stimulation signal, as described below. Embodiments of the present invention may employ the IMD 100 to perform afferent or efferent stimulation in combination with signal blocking, in order to treat medical conditions. Using the stimulation from the IMD 100, cranial nerve portions may be inhibited such that blocking of action potentials is achieved, wherein the various portions of the cranial nerve may also be stimulated to affect a mechanism in the patients' body.

The electrical stimulation treatment described herein may be used to treat a medical condition separately, or in combination with another type of treatment. For example, electrical stimulation treatment may be applied in combination with a chemical agent, such as various drugs, to treat various medical conditions. Therefore, various drugs may be taken by a patient, wherein the effects of these drugs may be enhanced by providing electrical stimulation to various portions of the nerves described herein to treat medical conditions. Further, the electrical stimulation may be performed in combination with treatment(s) relating to a biological or chemical agent. Therefore, drug therapy may be enhanced by the application of the stimulation provided by the IMD 100. The electrical stimulation treatment may also be performed in combination with other types of treatment, such as transcranial magnetic stimulation (TMS) treatment. Combining the electrical stimulation with the chemical, magnetic, or biological treatments, side effects associated with certain drugs or biological agents may be reduced.

Figure 2:
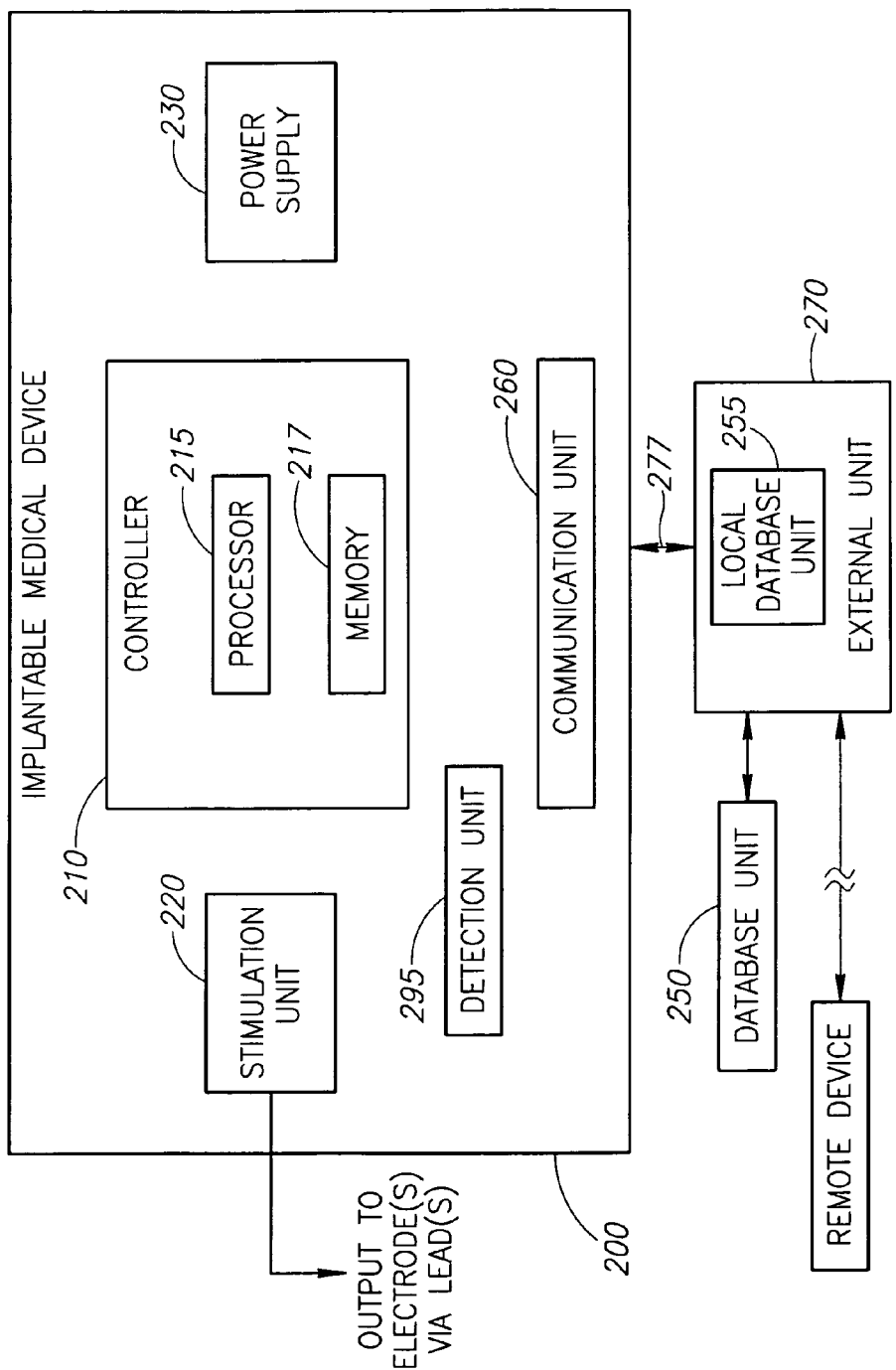
FIG. 2 is a block diagram of a medical device system that includes an implantable medical device and an external device for providing a patient management system for the implantable medical device, in accordance with one illustrative embodiment of the present invention.

Turning now to FIG. 2, a block diagram depiction of the IMD 200 is provided, in accordance with one illustrative embodiment of the present invention. The IMD 200 (such as generator 110 from FIG. 1) may comprise a controller 210 capable of controlling various aspects of the operation of the IMD 200. The controller 210 is capable of receiving internal data or external data and causing a stimulation unit 220 to generate and deliver an electrical signal to target tissues of the patient's body for treating a medical condition. For example, the controller 210 may receive manual instructions from an operator externally, or may cause the electrical signal to be generated and delivered based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM) dynamic random access memory (DRAM), electrically erasable programmable read-only memory (EEPROM), flash memory, etc.

The IMD 200 may also comprise a stimulation unit 220 capable of generating and delivering electrical signals to one or more electrodes via leads. A lead assembly such as lead assembly 122 (FIG. 1) may be coupled to the IMD 200. Therapy may be delivered to the leads comprising the lead assembly 122 by the stimulation unit 220 based upon instructions from the controller 210. The stimulation unit 220 may comprise various circuitry, such as electrical signal generators, impedance control circuitry to control the impedance "seen" by the leads, and other circuitry that receives instructions relating to the delivery of the electrical signal to tissue. The stimulation unit 220 is capable of delivering an electrical signal over the leads comprising the lead assembly 122.

The IMD 200 may also comprise a power supply 230. The power supply 230 may comprise a battery, voltage regulators, capacitors, etc., to provide power for the operation of the IMD 200, including delivering the therapeutic electrical signal. The power supply 230 comprises a power source that in some embodiments may be rechargeable. In other embodiments, a non-rechargeable power source may be used. The power supply 230 provides power for the operation of the IMD 200, including electronic operations and the electrical signal generation and delivery functions. The power supply 230 may comprise a lithium/thionyl chloride cell or a lithium/carbon monofluoride (LiCFx) cell. Other battery types known in the art of implantable medical devices may also be used.

The IMD 200 may also comprise a communication unit 260 capable of facilitating communications between the IMD 200 and various devices. In particular, the communication unit 260 is capable of providing transmission and reception of electronic signals to and from an external unit 270, such as computer 150 and wand 155 that may comprise an ED (FIG. 1). The communication unit 260 may include hardware, software, firmware, or any combination thereof.

The IMD 200 also comprises a detection unit 295 that is capable of detecting various patient parameters. For example, the detection unit 295 may comprise hardware, software, or firmware that is capable of obtaining and/or analyzing data relating to one or more body parameters of the patient, such as heart rate, cardiac cycle data, and/or respiratory cycle data. Based upon the data obtained by the detection unit 295, the IMD 200 may deliver the electrical signal to a portion of the vagus nerve to treat epilepsy, depression or other medical conditions. In one embodiment, the detection unit 295 may be capable of detecting a feedback response from the patient. The feedback response may include a magnetic signal input, a tap input, a wireless data input to the IMD 200, etc. The feedback may be indicative of a pain and/or noxious threshold, wherein the threshold may be the limit of tolerance of discomfort for a particular patient. The term "patient parameters" may refer to, but is not limited to, various body parameters, which may in some embodiments involve sensors coupled to the IMD 200.

In another embodiment, the detection unit 295 may comprise hardware, software, or firmware that is capable of obtaining and/or analyzing data relating to one or more body parameters of the patient's cardiac cycle. Based upon the data obtained by the detection unit 295, the IMD 200 may deliver the electrical signal to a portion of the vagus nerve at one or more particular points in the cardiac cycle to treat epilepsy, depression or other medical conditions.

The external unit 270 may be an ED that is capable of programming electrical signal parameters of the IMD 200. In one embodiment, the external unit 270 is a computer system capable of executing a data-acquisition program. The external unit 270 may be controlled by a healthcare provider, such as a physician, at a base station in, for example, a doctor's office. In alternative embodiments, the external unit 270 may be controlled by a patient in a system providing less control over the operation of the IMD 200 than another external unit 270 controlled by a healthcare provider. Whether controlled by the patient or by a healthcare provider, the external unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), an Apple-based computer system, etc. The external unit 270 may download various parameters and program software into the IMD 200 for programming the operation of the IMD, and may also receive and upload various status conditions and other data from the IMD 200. Communications between the external unit 270 and the communication unit 260 in the IMD 200 may occur via a wireless or other type of communication, represented generally by line 277 in FIG. 2. This may occur using, e.g., wand 155 (FIG. 1) to communicate by RF energy with a generator 110. Alternatively, the wand may be omitted in some systems, e.g., systems in which external unit 270 operates in the MICS bandwidths.

In one embodiment, the external unit 270 may comprise a local database unit 255. Optionally or alternatively, the external unit 270 may also be coupled to a database unit 250, which may be separate from external unit 270 (e.g., a centralized database wirelessly liked to a handheld external unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions using the external unit 270, which may include obtaining and/or analyzing data from the IMD 200 and/or data from the database unit 250 and/or the local database unit 255. The database unit 250 and/or the local database unit 255 may store various patient data such as heart rate data, cardiac cycle data (such as R-R interval data), respiratory cycle information, etc.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3:
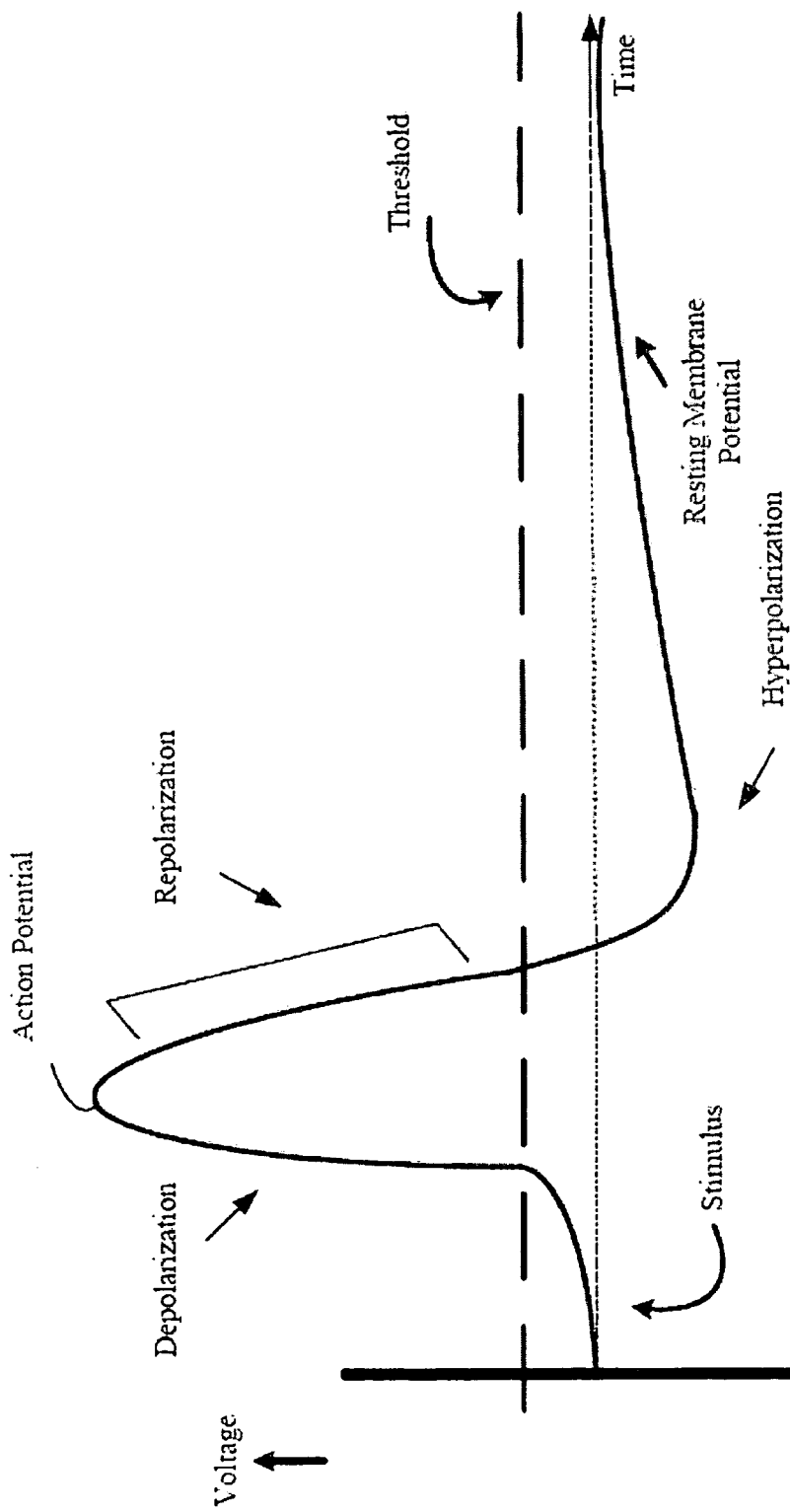
FIG. 3 illustrates an exemplary electrical signal of a firing neuron as a graph of voltage at a given location at particular times in response to application of an electrical signal to the nerve by the neurostimulator of FIG. 2, in accordance with one illustrative embodiment of the present invention.

FIG. 3 provides a stylized depiction of an exemplary electrical signal of a firing neuron as a graph of voltage at a given point on the nerve at particular times during the propagation of an action potential along the nerve, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur.

Figure 9:
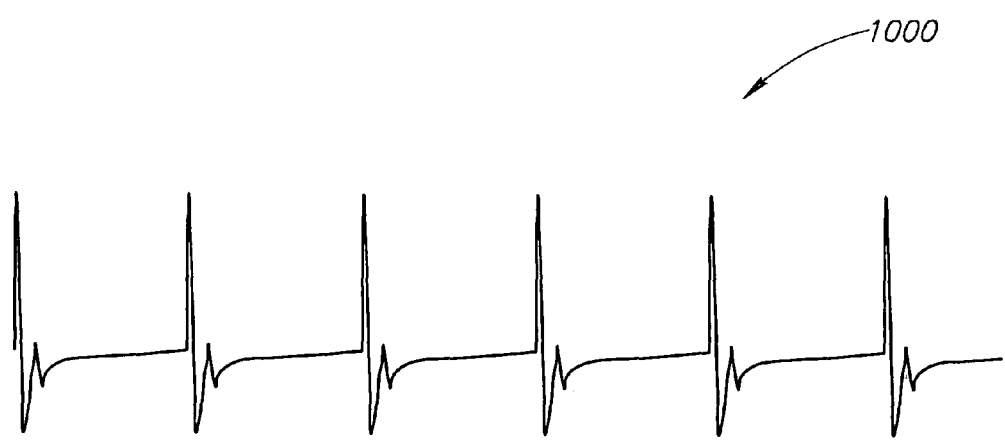
FIG. 9 illustrates a second pulse electrical signal that is not a Microburst signal.

Referring again to FIG. 1, the IMD 100 may generate a pulsed electrical signal in embodiments of the present invention for application to a cranial nerve such as vagus nerve 127 according to one or more programmed parameters. In one embodiment the electrical signal may be a conventional vagus nerve therapeutic electrical signal defined by a plurality of parameters such as current magnitude, pulse width, frequency, on-time and off-time. In another embodiment, the electrical signal may be a microburst signal defined by a plurality of parameters such as an interburst period, a number of a number of pulses per burst, an interpulse interval, a burst duration, a current magnitude, a pulse width, an on-time, and an off-time. In yet another embodiment, illustrated in FIG. 9, the electrical signal may comprise a first time period in which conventional vagus nerve therapeutic electrical signals 1000 are applied to the nerve, and a second time period in which microburst electrical signals are applied to the nerve. In a still further embodiment, conventional and microburst signals are alternated with a defined off-time in a conventional on-time and a microburst on-time. Thus a 30 second burst of a conventional VNS signal may be followed by 5 minutes off-time, followed by a 1 minute period of microburst stimulation, followed by a 5 minute off-time, after which the process repeats itself.

Figure 4C:
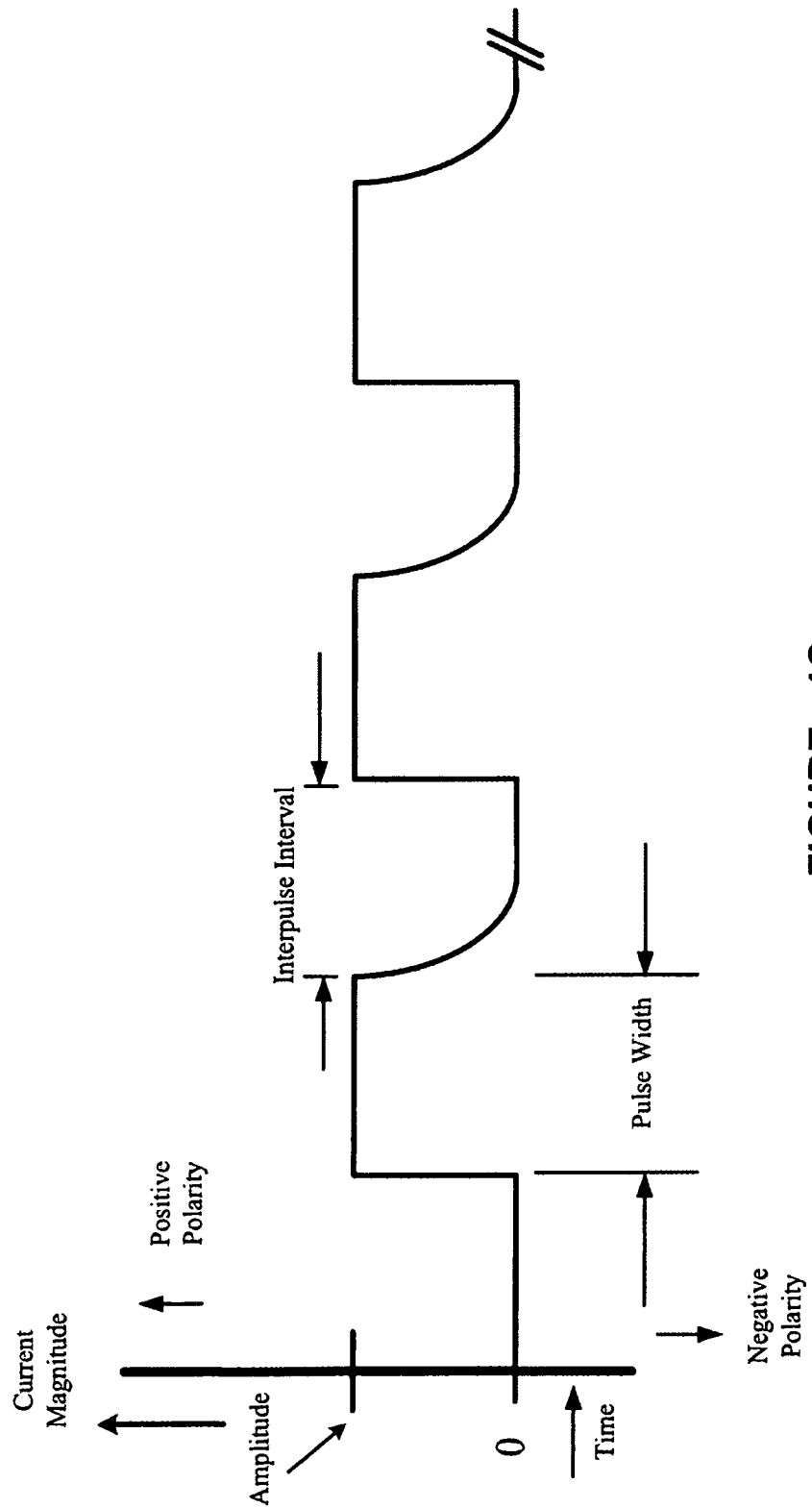

Exemplary pulse waveforms in accordance with one embodiment of the present invention are shown in FIGS. 4A-4C. Pulse shapes in electrical signals according to the present invention may include a variety of shapes known in the art including square waves, biphasic pulses (including active and passive charge-balanced biphasic pulses), triphasic waveforms, etc. In one embodiment, the pulses comprise a square, biphasic waveform in which the second phase is a charge-balancing phase of the opposite polarity to the first phase.

In addition to conventional programmed or random off-time periods (and whether conventional or microburst stimulation is applied), the duration of a period of "off-time" in embodiments of the present invention may be varied with changes in the patient's cardiac cycle. In one embodiment, the "off-time" begins about 10 msec to about 800 msec after the onset of the R-wave of a patient's cardiac cycle and ends at the onset of the R-wave of a later cardiac cycle of the patient, such as the next cardiac cycle.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode may be coupled to each of the vagus nerves 127 or a branch of either vagus nerve. The term "operatively" coupled may include directly or indirectly coupling. Each of the nerves in this embodiment or others involving two or more cranial nerves may be stimulated according to particular activation modalities that may be independent between the two nerves.

Another activation modality for stimulation is to program the output of the IMD 100 to the maximum amplitude which the patient may tolerate. The stimulation may be cycled on and off for a predetermined period of time followed by a relatively long interval without stimulation. Where the cranial nerve stimulation system is completely external to the patient's body, higher current amplitudes may be needed to overcome the attenuation resulting from the absence of direct contact with the cranial nerve and the additional impedance of the skin of the patient. Although external systems typically require greater power consumption than implantable ones, they have an advantage in that their batteries may be replaced without surgery.

Returning to systems for providing cranial nerve stimulation, such as that shown in FIGS. 1 and 2, stimulation may be provided in either non-feedback or feedback modalities. Where cranial nerve stimulation is provided based solely on programmed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. The patient may manually activate the IMD 100 to stimulate the vagus nerve 127 to treat an acute episode of a medical condition. The patient may also be permitted to alter the intensity of the signals applied to the cranial nerve within limits established by the physician.

Patient activation of an IMD 100 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 110 may include a sensor such as piezoelectric element mounted to the inner surface of the generator case and adapted to detect light taps by the patient on the implant site. One or more taps applied in fast sequence to the skin above the location of the electrical signal generator 110 in the patient's body may be programmed into the implanted medical device 100 as a signal for activation of the electrical signal generator 110. Two taps spaced apart by a slightly longer duration of time may be programmed into the IMD 100 to indicate a desire to deactivate the electrical signal generator 110, for example. The patient may be given limited control over operation of the device to an extent which may be determined by the program dictated or entered by the attending physician. The patient may also activate the IMD 100 using other suitable techniques or apparatus.

In some embodiments, feedback stimulation systems other than manually-initiated stimulation may be used in the present invention. A cranial nerve stimulation system may include a sensing lead coupled at its proximal end to a header along with a stimulation lead and electrode assemblies. A sensor may be coupled to the distal end of the sensing lead. The sensor may include a cardiac cycle sensor. The sensor may also include a nerve sensor for sensing activity on a nerve, such as a cranial nerve, such as the vagus nerve 127.

In one embodiment, the sensor may sense a body parameter that corresponds to a symptom of a medical condition. If the sensor is to be used to detect a symptom of the medical condition, a signal analysis circuit may be incorporated into the IMD 100 for processing and analyzing signals from the sensor. Upon detection of the symptom of the medical condition, the processed digital signal may be supplied to a microprocessor in the IMD 100 to trigger application of the electrical signal to the cranial nerve, such as the vagus nerve 127. In another embodiment, the detection of a symptom of interest may trigger a stimulation program including different stimulation parameters from a passive stimulation program. This may entail providing a higher current stimulation signal or providing a higher ratio of on-time to off-time.

Figure 5:
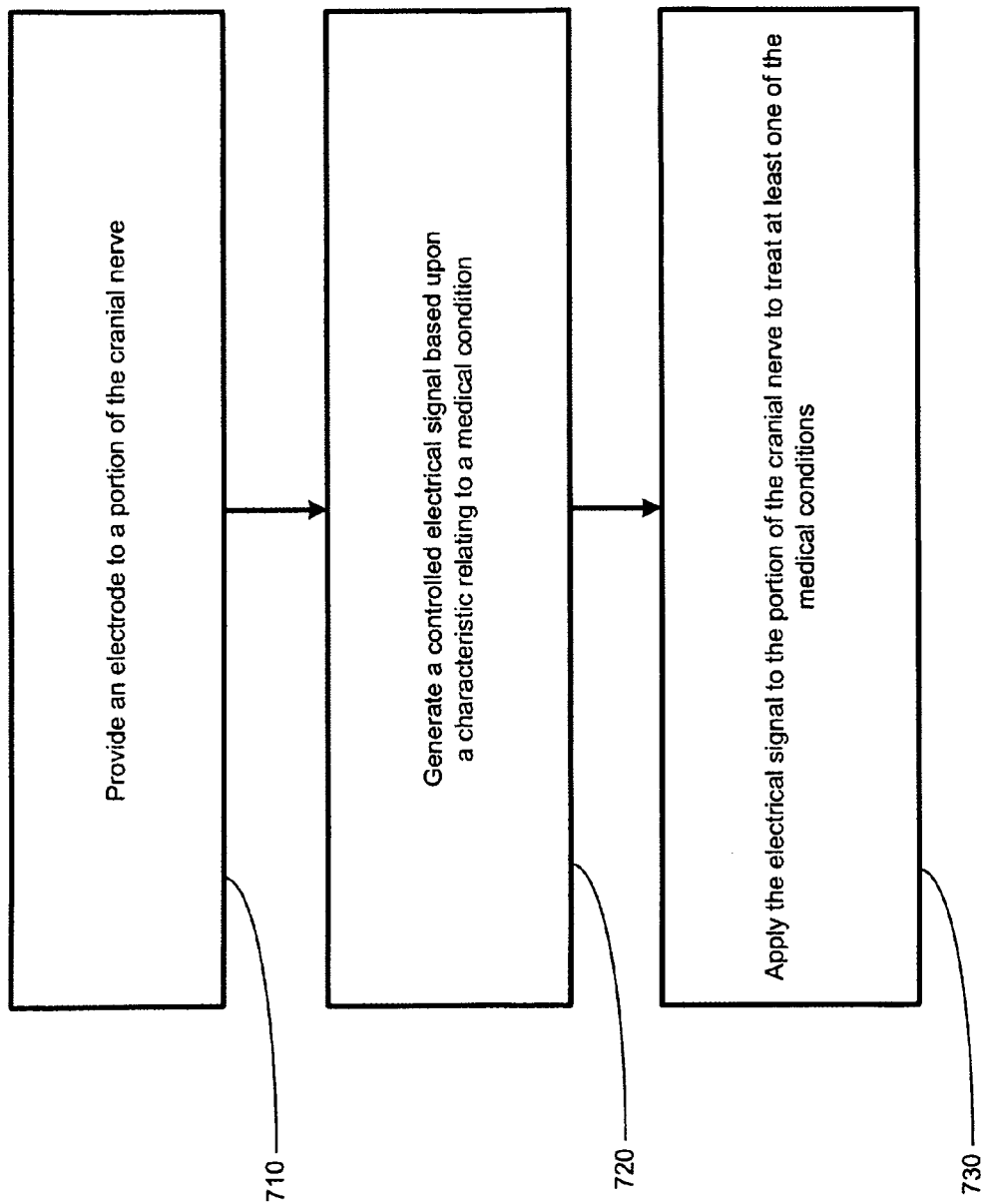
FIG. 5 illustrates a flowchart depiction of a method for treating a medical condition, in accordance with an illustrative embodiment of the present invention.

Turning now to FIG. 5, a flowchart depiction of a method for treating a medical condition, in accordance with one illustrative embodiment of the present invention is provided. An electrode may be coupled to a portion of a cranial nerve to perform a stimulation function or a blocking function to treat a medical condition. In one embodiment, one or more electrodes may be positioned in electrical contact or proximate to a portion of the cranial nerve to deliver a stimulation signal to the portion of the cranial nerve (block 710). The electrodes may be operatively coupled to at least one of main trunk of the right or left vagus nerve, or any branch thereof. The IMD 100 may then generate a controlled electrical signal, based upon one or more characteristics relating to the medical condition(s) of the patient (block 720). This may include a predetermined electrical signal that is preprogrammed based upon a particular condition of a patient. The term "medical condition" may include epilepsy or depression, among others. For example, a physician may pre-program the type of stimulation to provide (e.g., conventional stimulation, microburst stimulation, or combination conventional/microburst stimulation) in order to treat the patient based upon the medical condition of the patient. The IMD 100 may then generate a signal, such as a controlled-current pulse signal, to affect one or more portions of the neurological system of a patient.

The IMD 100 may then deliver the stimulation signal to the portion of the cranial nerve (block 730). The application of the electrical signal may be delivered to the main trunk of the right or left vagus nerve, or any branch thereof. In one embodiment, application of the stimulation signal may be designed to generate afferent electrical activity on the vagus nerve 127. Further, the stimulation by the IMD 100 may reduce incidents or symptoms relating to a medical condition. Application of the stimulation signal may be controlled so that the signal is applied during periods of the cardiac cycle correlated with increased afferent traffic on the cranial nerve.

In another embodiment, application of the stimulation signal may be designed to promote a blocking effect relating to a signal that is being sent from the brain, to treat the medical condition. This may be accomplished by delivering a particular type of controlled electrical signal, such as a controlled current signal to the cranial nerve. In yet another embodiment, afferent fibers may also be stimulated in combination with an efferent blocking to treat a medical condition.

Additional functions, such as a detection process, may be alternatively employed with the embodiment of the present invention. The detection process may be employed such that an external detection or an internal detection of a bodily function may be used to adjust the operation of the IMD 100.

Figure 6:
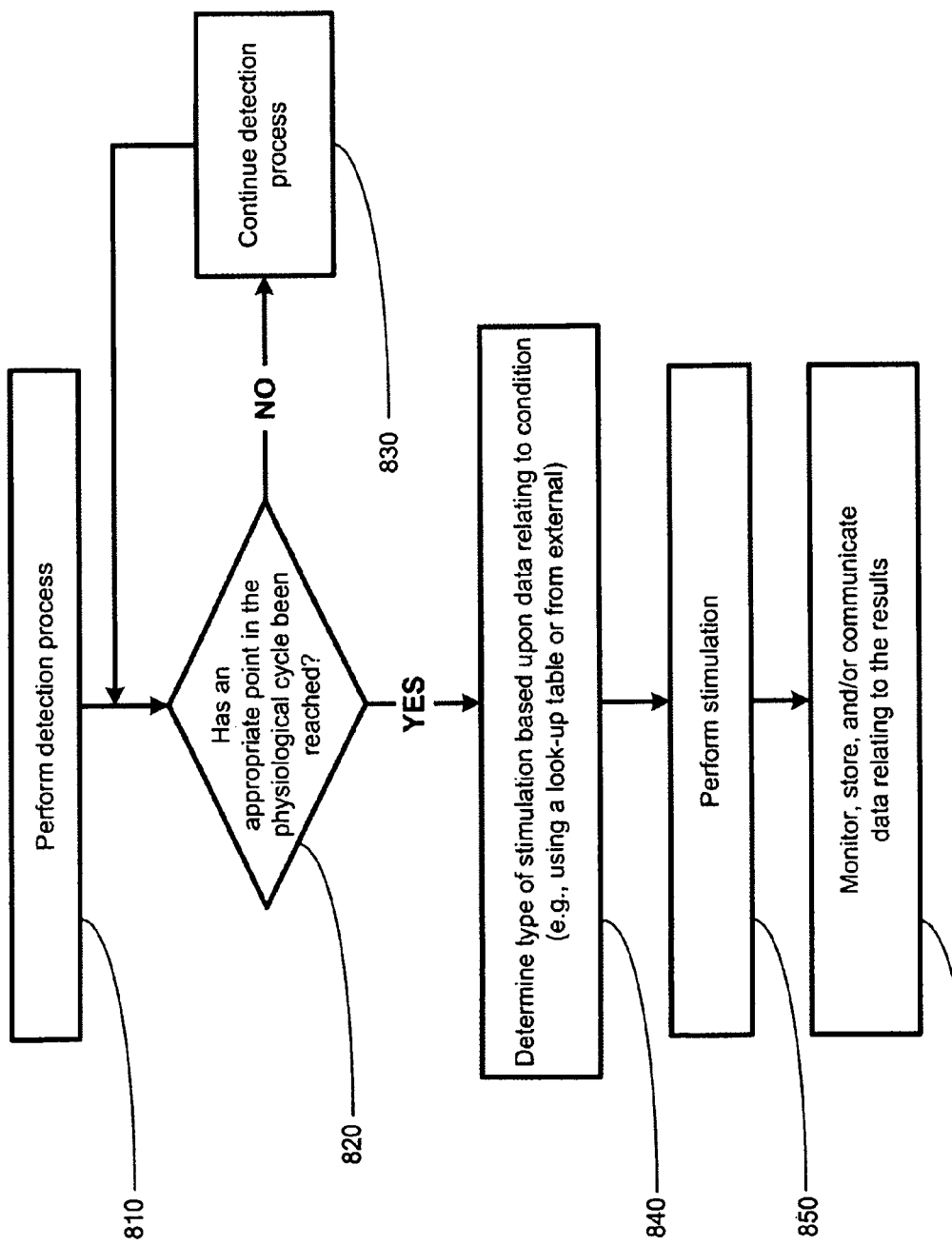
FIG. 6 illustrates a flowchart depiction of an alternative method for treating a medical condition, in accordance with an alternative illustrative embodiment of the present invention.

Turning now to FIG. 6, a block diagram depiction of a method in accordance with an alternative embodiment of the present invention is illustrated. The IMD 100 may perform a detection process, which may include checking a database for physiological data, such as data indicative of the patient's cardiac cycle (block 810). Data from the database may be used for determining the timing of the delivery of stimulation signals, e.g. timing delivery based on the patient's cardiac cycle. The detection process may encompass detecting a variety of types of characteristics of the cardiac cycle of the patient. A more detailed depiction of the steps for performing the detection process is provided in FIG. 7, and accompanying description below. Upon performing the detection process, the IMD 100 may determine whether an appropriate point in the cardiac cycle has been reached (block 820). Upon a determination that an appropriate point in the cardiac cycle has not been reached, the detection process is continued (block 830).

Upon a determination that an appropriate time in the cardiac cycle has been reached, a determination as to the type of stimulation based upon data relating to the medical condition is made (block 840). The type of stimulation may be determined in a variety of manners, such as performing a look-up in a look-up table that may be stored in the memory 217. Alternatively, the type of stimulation may be determined by an input from an external source, such as the external unit 270 or an input from the patient. Further, determination of the type of stimulation may also include determining the location as to where the stimulation is to be delivered. Accordingly, the selection of particular electrodes, which may be used to deliver the stimulation signal, is made.

Upon determining the type of stimulation to be delivered, the IMD 100 performs the stimulation by applying the electrical signal to one or more selected electrodes (block 850). Upon delivery of the stimulation, the IMD 100 may monitor, store, or compute the results of the stimulation (block 860). For example, based upon the calculation, a determination may be made that adjustment(s) to the type of signal to be delivered for stimulation, may be performed. Further, the calculations may reflect the need to deliver additional stimulation. Additionally, data relating to the results of stimulation may be stored in memory 217 for later extraction or further analysis. Also, in one embodiment, real time or near real time communications may be provided to communicate the stimulation result or the stimulation log to an external unit 270.

Figure 7:
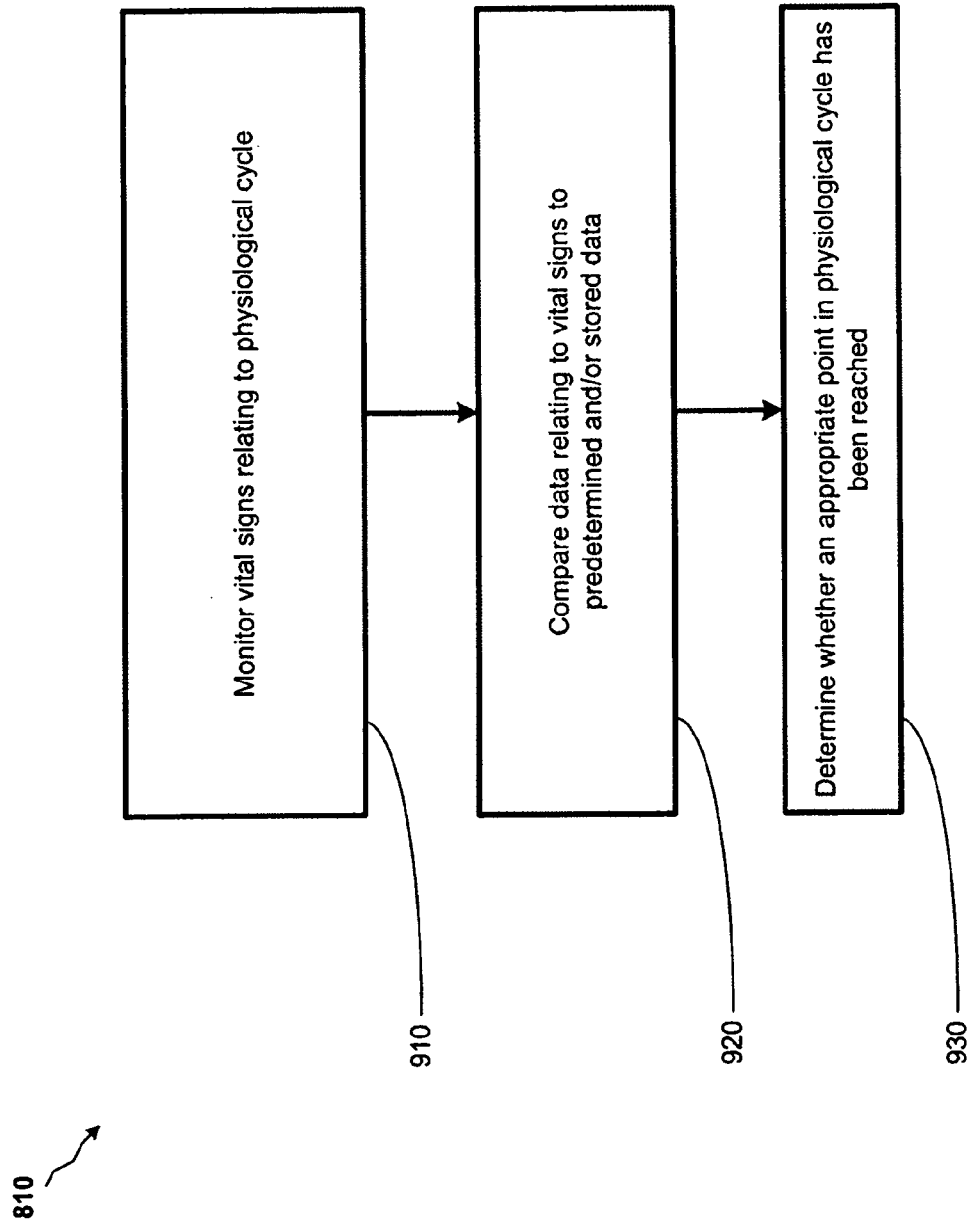
FIG. 7 depicts a more detailed flowchart depiction of the step of performing a detection process of FIG. 6, in accordance with an illustrative embodiment of the present invention.

Turning now to FIG. 7, a more detailed block diagram depiction of a particular embodiment of the step of performing the detection process of block 810 in FIG. 6, is illustrated. The system 100 may monitor one or more signals relating to the cardiac cycle of the patient (block 910). This detection may be made by sensors residing inside the human body, which may be operatively coupled to the IMD 100. In a particular embodiment, the sensors may be located in the IMD 100. In another embodiment, these signals may be detected by external means and may be provided to the IMD 100 from an external device via the communication unit 260.

Upon acquisition of various signals, a comparison may be performed comparing the data relating to the real-time signals or stored physiological data to predetermined and/or stored data (block 920). For example, an ECG may be compared to various benchmark ECGs to determine whether a portion of the cardiac cycle correlated with increased afferent vagus nerve conduction has been reached. Based upon the comparison of the collected data with theoretical, stored thresholds, the IMD 100 may determine whether an appropriate time to commence an on-time (i.e., a time to apply the electrical signal to the cranial nerve) has been reached (block 930). Based upon the determination described in FIG. 7, the IMD 100 may continue to determine whether the medical condition is sufficiently significant to perform treatment, as described in FIG. 6.

Additionally, external devices may perform such calculation and communicate the results or accompanying instructions to the IMD 100. The IMD 100 may also determine the specific cranial nerve(s), or the location or branch of the nerve(s), to stimulate. The IMD 100 may also indicate the type of treatment to be delivered. For example, an electrical treatment alone or in combination with another type of treatment may be provided based upon the quantifiable parameter(s) that are detected. For example, a determination may be made that an electrical signal by itself is to be delivered. Alternatively, based upon a particular type of medical condition, a determination may be made that an electrical signal, in combination with a magnetic signal, such as transcranial magnetic stimulation (TMS) may be performed. Stimulation can be induced by light such as from a laser.

In addition to electrical or magnetic stimulation, a determination may be made whether to deliver a chemical, biological, or other type of treatment(s) in combination with the electrical stimulation provided by the IMD 100. In one example, electrical stimulation may be used to enhance the effectiveness of a chemical agent. Therefore, various drugs or other compounds may be delivered in combination with an electrical stimulation or a magnetic stimulation. Based upon the type of stimulation to be performed, the IMD 100 delivers the stimulation to treat various medical conditions.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit, and scope of the invention, as defined by the appended claims. It should be especially apparent that the principles of the invention may be applied to selected cranial nerves other than, or in addition to, the vagus nerve to achieve particular results in treating patients having epilepsy, depression, or other conditions.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method of treating a medical condition in a patient having a brain, a vagus nerve, a trigeminal nerve, a glossopharyngeal nerve, a cardiac cycle, and a respiratory cycle, the method comprising:

detecting a first selected portion of at least one of the cardiac cycle of the patient and the respiratory cycle of the patient; and applying a first pulsed electrical signal to at least one of the vagus nerve, the trigeminal nerve, and the glossopharyngeal nerve to modulate the brain of the patient in response to detecting the first selected portion of the at least one of the cardiac cycle and the respiratory cycle of the patient, the first pulsed electrical signal comprising a plurality of microbursts wherein each microburst is separated from an adjacent microburst by an interburst period of at least 100 milliseconds, and each microburst comprises:

2 pulses to 20 pulses;

an interpulse interval between adjacent pulses of the microburst of from about 1 millisecond to about 20 milliseconds; and a microburst duration of not greater than 1 second, wherein the first pulsed electrical signal is configured to generate afferent electrical activity on the at least one of the vagus nerve, the trigeminal nerve, and the glossopharyngeal nerve that produces a first enhanced evoked potential in the brain of the patient;

measuring the first enhanced evoked potential in the brain of the patient;

changing at least one of the interburst period, the number of pulses per microburst, the interpulse interval between adjacent pulses of the microburst, and the microburst duration to provide a second pulsed electrical signal;

detecting a second selected portion of the at least one of the cardiac cycle of the patient and the respiratory cycle of the patient;

applying the second pulsed electrical signal to the at least one of the vagus nerve, the trigeminal nerve, and the glossopharyngeal nerve to modulate the brain of the patient in response to detecting the second selected portion of the at least one of the cardiac cycle and the respiratory cycle of the patient, wherein the second pulsed electrical signal is configured to generate afferent electrical activity on the at least one of the vagus nerve, the trigeminal nerve, and the glossopharyngeal nerve that produces a second enhanced evoked potential in the brain of the patient;

measuring the second enhanced evoked potential in the brain of the patient;

comparing the first enhanced evoked potential to the second enhanced evoked potential;

selecting one of the first pulsed electrical signal and the second pulsed electrical signal for continued application to the at least one of the vagus nerve, the trigeminal nerve, and the glossopharyngeal nerve based upon the comparison between the first and second enhanced evoked potentials; and applying the selected pulsed electrical signal to the at least one of the vagus nerve, the trigeminal nerve, and the glossopharyngeal nerve of the patient.

2. The method of claim 1 wherein the steps of detecting the first and second selected portions of at least one of the cardiac cycle of the patient and the respiratory cycle of the patient comprise determining a heart rate variability parameter, and wherein the steps of applying the first and second pulsed electrical signals to the at least one of the vagus nerve, the trigeminal nerve, and the glossopharyngeal nerve further comprise applying the first and second pulsed electrical signals to the at least one of the vagus nerve, the trigeminal nerve, and the glossopharyngeal nerve in response to having determined the heart rate variability parameter.

3. The method of claim 1, further comprising increasing a heart rate variability parameter of the patient by applying the first and second pulsed electrical signals to the at least one of the vagus nerve, the trigeminal nerve, and the glossopharyngeal nerve.

4. The method of claim 1, wherein the steps of detecting the first and second portions of at least one of the cardiac cycle of the patient and the respiratory cycle of the patient comprise detecting an inhibition phase of the cardiac cycle, and wherein the steps of applying the first and second pulsed electrical signals to the at least one of the vagus nerve, the trigeminal nerve, and the glossopharyngeal nerve comprises not applying the first and second pulsed electrical signals during the inhibition phase of the cardiac cycle.

5. The method of claim 1 wherein the steps of detecting the first and second selected portions of at least one of the cardiac cycle of the patient and the respiratory cycle of the patient comprise detecting an R-wave portion of a selected cardiac cycle of the patient, and wherein the steps of applying the first and second pulsed electrical signals to the at least one of the vagus nerve, the trigeminal nerve, and the glossopharyngeal nerve comprise applying the first and second pulsed electrical signals after a delay period following the detection of the R-wave portion of the selected cardiac cycle, and not applying a signal for a period that comprises a remaining portion of the same selected cardiac cycle and one or more subsequent cardiac cycles.

6. The method of claim 1 wherein the steps of detecting the first and second selected portions of at least one of the cardiac cycle of the patient and the respiratory cycle of the patient comprise detecting at least a portion of the cardiac cycle comprising a P wave, an R wave, an R-R interval, a QRS complex, a T wave, or the entire PQRST cycle.

7. The method of claim 1 further comprising sensing a temperature of the patient, wherein the steps of applying the first and second pulsed electrical signals to the at least one of the vagus nerve, the trigeminal nerve, and the glossopharyngeal nerve comprise applying the first and second pulsed electrical signals in response to the sensed temperature.

8. The method of claim 1 further comprising applying a third pulsed electrical signal to the at least one of the vagus nerve, the trigeminal nerve, and the glossopharyngeal nerve without reference to the at least one of the cardiac cycle of the patient and the respiratory cycle of the patient.

9. The method of claim 8 wherein the third pulsed electrical signal does not comprise a plurality of microbursts.

10. The method of claim 1 wherein the steps of detecting the first and second selected portions of at least one of the cardiac cycle of the patient and the respiratory cycle of the patient comprises detecting an inhibition phase of the respiratory cycle, and wherein the steps of applying the first and second pulsed electrical signals to the at least one of the vagus nerve, the trigeminal nerve, and the glossopharyngeal nerve comprise not applying the first and second pulsed electrical signals during the inhibition phase of the respiratory cycle.

11. The method of claim 1 wherein the steps of detecting the first and second selected portions of at least one of the cardiac cycle of the patient and the respiratory cycle of the patient comprise detecting a beginning of inspiration of a selected respiratory cycle of the patient, and wherein the steps of applying the first and second pulsed electrical signals to the at least one of the vagus nerve, the trigeminal nerve, and the glossopharyngeal nerve comprise applying the first and second pulsed electrical signals after a delay period following the detection of the beginning of inspiration, and not applying a signal for a period that comprises a remaining portion of the same selected respiratory cycle and one or more subsequent respiratory cycles.

12. The method of claim 1 wherein the detected first and second selected portions of at least one of the cardiac cycle of the patient and the respiratory cycle of the patient comprise a portion of the respiratory cycle of the patient when inspiration occurs, and wherein the steps of detecting the first and second selected portions of the respiratory cycle of the patient when inspiration occurs comprise using a high frequency component of the heart rate variability power spectrum to determine when inspiration occurs.

13. The method of claim 1 wherein the steps of detecting the first and second selected portions of at least one of the cardiac cycle of the patient and the respiratory cycle of the patient comprise detecting at least a portion of the cardiac cycle of the patient by sensing electrical activity on the at least one of the vagus nerve, the trigeminal nerve, and the glossopharyngeal nerve and applying the first and second pulsed electrical signals when the electrical activity increases.

14. The method of claim 1, wherein the first and second pulsed electrical signals are configured to increase afferent activity on the at least one of the vagus nerve, the trigeminal nerve, and the glossopharyngeal nerve to be conducted thereby to the patient's brain.

15. The method of claim 14, further comprising:
applying a blocking signal to the at least one of the vagus nerve, the trigeminal nerve, and the glossopharyngeal nerve, the blocking signal being configured to block efferent electrical activity on the at least one of the vagus nerve, the trigeminal nerve, and the glossopharyngeal nerve.

16. A method of treating a medical condition in a patient comprising a brain, a vagus nerve, a trigeminal nerve, a glossopharyngeal nerve, and a respiratory cycle, the method comprising:
detecting a first selected portion of the respiratory cycle of the patient; and
applying a first pulsed electrical signal comprising a plurality of microbursts to at least one of the vagus nerve, the trigeminal nerve, and the glossopharyngeal nerve to modulate the brain of the patient in response to detecting the first selected portion of the respiratory cycle of the patient, the first pulsed electrical signal comprising a plurality of microbursts, wherein each microburst is separated from an adjacent microburst by an interburst period of at least 100 milliseconds and comprises:
2 pulses to 20 pulses;
an interpulse interval between adjacent pulses of the microburst of from about 1 millisecond to about 20 milliseconds; and
a microburst duration of not greater than 1 second,
wherein the first pulsed electrical signal is configured to generate afferent electrical activity on the at least one of the vagus nerve, the trigeminal nerve, and the glossopharyngeal nerve that produces a first enhanced evoked potential in the brain of the patient;
measuring the first enhanced evoked potential in the brain of the patient;
changing at least one of the interburst period, the number of pulses per microburst, the interpulse interval between adjacent pulses of the microburst, and the microburst duration to provide a second pulsed electrical signal;
detecting a second selected portion of the at least one of the cardiac cycle of the patient and the respiratory cycle of the patient;
applying the second pulsed electrical signal to the at least one of the vagus nerve, the trigeminal nerve, and the glossopharyngeal nerve to modulate the brain of the patient in response to detecting the second selected portion of the at least one of the cardiac cycle and the respiratory cycle of the patient, wherein the second pulsed electrical signal is configured to generate afferent electrical activity on the at least one of the vagus nerve, the trigeminal nerve, and the glossopharyngeal nerve that produces a second enhanced evoked potential in the brain of the patient;
measuring the second enhanced evoked potential in the brain of the patient;
comparing the first enhanced evoked potential to the second enhanced evoked potential;
selecting one of the first pulsed electrical signal and the second pulsed electrical signal for continued application to the at least one of the vagus nerve, the trigeminal nerve, and the glossopharyngeal nerve based upon the comparison between the first and second enhanced evoked potentials; and
applying the selected pulsed electrical signal to the at least one of the vagus nerve, the trigeminal nerve, and the glossopharyngeal nerve of the patient.

\* \* \* \* \*